(12) United States Patent
Fontaine et al.

(10) Patent No.: US 10,786,560 B1
(45) Date of Patent: Sep. 29, 2020

(54) STREPTOCOCCUS AGALACTIAE ANTIGENS ASSOCIATED WITH STRAINS VIRULENT IN FISH

(71) Applicant: Moredun Research Institute, Penicuik, Midlothian (GB)

(72) Inventors: Michael Fontaine, Edinburgh (GB); Ruth Nicolet Zadoks, Edinburgh (GB); Christian Marie Joseph Delannoy, Edinburgh (GB)

(73) Assignee: MOREDUN RESEARCH INSTITUTE, Penicuik, Midlothian (GB)

( * ) Notice: Subject to any disclaimer, the term of this patent is extended or adjusted under 35 U.S.C. 154(b) by 284 days.

(21) Appl. No.: 15/508,327

(22) PCT Filed: Sep. 3, 2015

(86) PCT No.: PCT/GB2015/052542
§ 371 (c)(1),
(2) Date: Mar. 2, 2017

(87) PCT Pub. No.: WO2016/034879
PCT Pub. Date: Mar. 10, 2016

(30) Foreign Application Priority Data

Sep. 3, 2014 (GB) ..................................... 1415602

(51) Int. Cl.
*A61K 39/00* (2006.01)
*A61K 39/09* (2006.01)
*C07K 16/12* (2006.01)
*C07K 16/40* (2006.01)
*C12Q 1/689* (2018.01)

(52) U.S. Cl.
CPC ........ *A61K 39/092* (2013.01); *C07K 16/1275* (2013.01); *C07K 16/40* (2013.01); *C12Q 1/689* (2013.01); *C12Y 302/01022* (2013.01); *C12Y 401/02019* (2013.01); *C12Y 501/03003* (2013.01); *A61K 2039/53* (2013.01); *A61K 2039/57* (2013.01); *C12Q 2600/158* (2013.01)

(58) Field of Classification Search
CPC .................................................. A61K 39/092
See application file for complete search history.

(56) References Cited

U.S. PATENT DOCUMENTS

2010/0105865 A1 * 4/2010 Telford ................ C07K 14/315 530/350
2012/0258139 A1 10/2012 Pridgeon et al.

OTHER PUBLICATIONS

International Search Report and Written Opinion, PCT/GB2015/052542, dated Feb. 18, 2016, 18 pages.
Pereira UP et al. In silico prediction of conserved vaccine targets in *Streptococcus agalactiae* strains isolated from fish, cattle, and human samples. Genetics and Molecular Research. Jan. 1, 2013; 12(3): 2902-2912.
Noraini O et al. Efficacy of spray administration of formalin-killed *Streptococcus agalactiae* in hybrid red tipapia. Journal of Aquatic Animal Health. Jun. 1, 2013; 35(2): 142-148.
Chen M et al. Screening vaccine candidate strains against *Streptococcus agalactiae* of tilapia based on PFGE genotype. Vaccine. Sep. 14, 2012; 30(42): 6088-6092.
Pasnik DJ et al. Passive immunization of Nile tilapia (*Oreochromis niloticus*) provides significant protection against *Streptococcus agalactiae*. Fish & Shellfish Immunology. Oct. 1, 2006; 21: 365-371.
Search Report corresponding to United Kingdom Application No. GB1415602.0, dated May 18, 2015, 5 pages.
Zirnstein et al., Characterization and analysis of the galactose galM (mutarotase) gene from *Streptococcus thermophiles*, Journal of Dairy Science, vol. 79, Suppl. 1, 1996, p. 123, Abstract D147.
Vaillancourt et al., Role of galK and galM in Galactose Metabolism by *Streptococcus thermmophilus*, Applied and Environmental Microbiology, vol. 74, Issue 4, 2008, pp. 1264-1267.
Teska et al., Non-haemolytic group B streptococci from humans, fish, and frogs, Biomedical Letters, vol. 5, Issue 199, 1994, pp. 195-201, Abstract.
Rubens et al., Identification of cpsD a gene essential for type III capsule expression in group B streptococci, Molecular Microbiology, vol. 8, Issue 5, 1993, pp. 843-855, Abstract.
Poolman et al., Carbohydrate Utilization in *Streptococcus thermophiles*: Characterization of the Genes for Aldose 1-Epimerase (Mutarotase) and UDPglucose 4-Epimerase, Journal of Bacteriology, vol. 172, Issue 7, 1990, pp. 4037-4047.
Delannoy et al., Human *Streptococcus agalactiae* strains in aquatic mammals and fish, BMC Microbiology, vol. 13, 2013, p. 7, col. 1.
Anbukkarasi et al., Assessment of expression of Leloir pathway genes in wild-type galactose-germenting *Streptococcus themophilus* by real-time PCR, European Food Research and Technology, vol. 239, Issue 5, 2014, pp. 895-903.

* cited by examiner

*Primary Examiner* — Albert M Navarro
(74) *Attorney, Agent, or Firm* — Myers Bigel, P.A.

(57) ABSTRACT

The present disclosure is based upon the identification of a number of *Streptococcus agalactiae* genes which are required for virulence in fish species. Specifically, the disclosure relates to genomic content present in fish-associated *S. agalactiae* strains that is absent from strains which are non-virulent to fish. Further disclosed is the use of a number of *S. agalactiae* proteins and antigens in methods, immunogenic compositions and vaccines for raising immune responses and treating or preventing diseases, conditions and/or infections with a Streptococcal aetiology.

Figure 1:
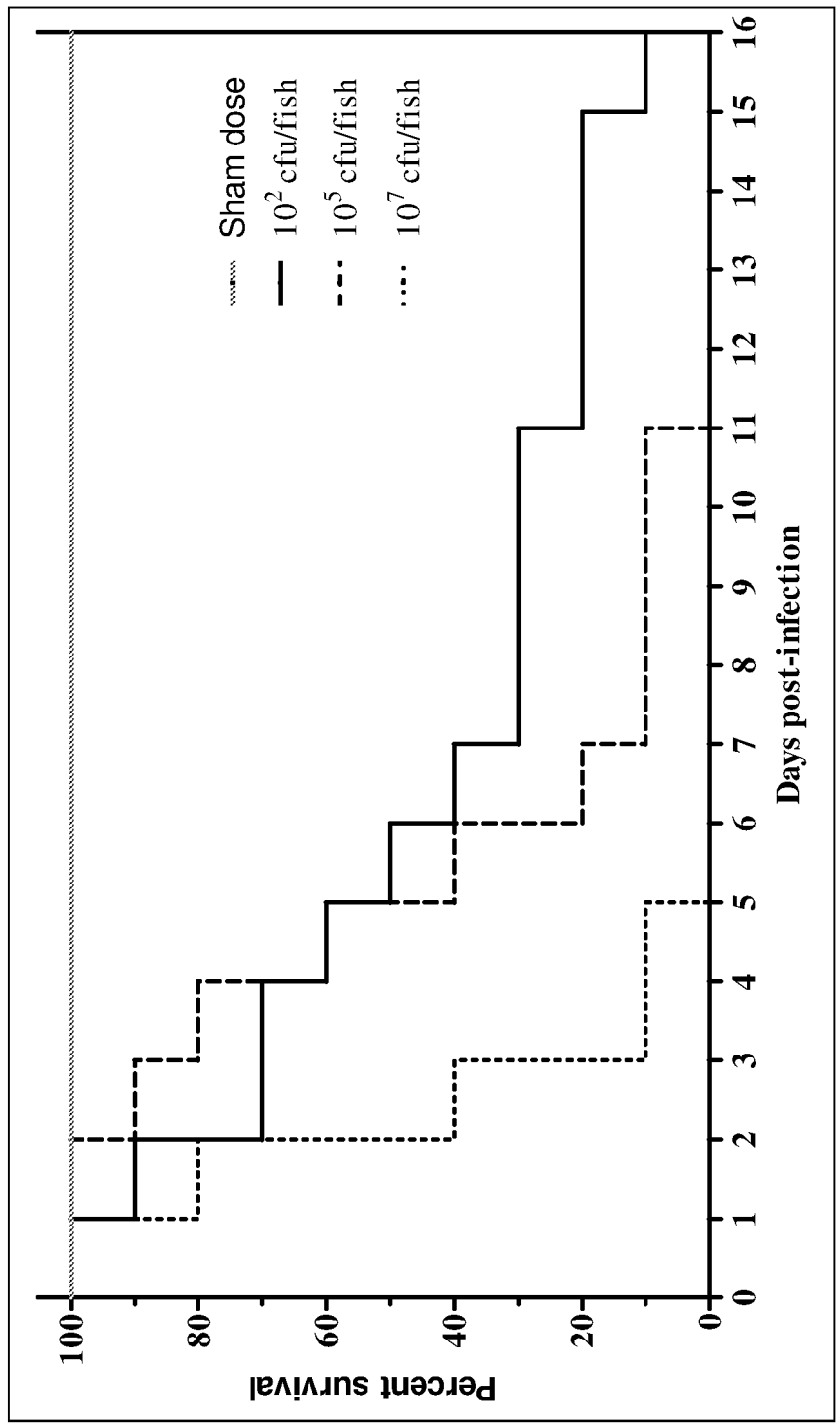

4 Claims, 5 Drawing Sheets
Specification includes a Sequence Listing.

SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
aaataatccg attgttcctg                           20

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
atattactat aaatttccct tctaa                     25

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ctatgccgaa gatgattatt tg                        22

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
cttcttggcg tagttccttc agta                      24

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
aaatcggcaa gcagacagaa aatgaat                   27

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
gcaatagcac aaccgccaaa acc                       23

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
aagggtgcta gtagtgccga acattaat                  28

<210> SEQ ID NO 8
<211> LENGTH: 27
<212> TYPE: DNA

<213> ORGANISM: Artificial Sequence
<220> FEATURE:
<223> OTHER INFORMATION: Primer

<400> SEQUENCE: 8
aaccagccat catccataac aaaaagt					27

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9
attggtattt ggagcactgt agg					23

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
tcttatttat aggccggact tgta					24

<210> SEQ ID NO 11
<211> LENGTH: 159
<212> TYPE: DNA
<213> ORGANISM: Streptococcus agalactiae

<400> SEQUENCE: 11
gtagggttac tacaacgaaa caaagagtaa aaatccgtta ttttaagcat ttcttcaagc					60 attttgtctt tgttgaagaa ggtgatttga caccaaaaag gtattaaaaa acatattgac					120 gtgaccgttt gttttgaagt ggcttgcgta gacaaaaaa					159

<210> SEQ ID NO 12
<211> LENGTH: 160
<212> TYPE: DNA
<213> ORGANISM: Streptococcus agalactiae

<400> SEQUENCE: 12
gtagcgttgc tacaacgaag caaagggtaa aaatccttta ttttaagcac tttttcaagc					60 attttgtctt tattgaaaag agtgatttta acataaaaaa ggtattaaaa aacatattga					120 cgtgaccgtt tgttttgaag tggcttgcgt agacaaaaaa					160

<210> SEQ ID NO 13
<211> LENGTH: 159
<212> TYPE: DNA
<213> ORGANISM: Streptococcus agalactiae

<400> SEQUENCE: 13
gtagggttac tacaacgaaa caaagagaaa aatcctgcat tttaagtagt tttacaagca					60 ttttgtcttt gttgaagaag gtgaatttga caccaaaaag gtatcaaaaa acatattgaa					120 gtgaccgttt gtttagatgt tgattgcgta gacaaaaag					159

STREPTOCOCCUS AGALACTIAE ANTIGENS ASSOCIATED WITH STRAINS VIRULENT IN FISH

FIELD OF THE INVENTION

The present invention relates to *Streptococcus agalactiae* genes which are required for virulence in fish species. Specifically, the invention provides a selection of fish-associated *S. agalactiae* nucleic acid/amino acid sequences which have application in methods of detecting *S. agalactiae* strains which are pathogenic in fish, diagnostic procedures, methods of raising immune responses, vaccines and the like.

BACKGROUND OF THE INVENTION

*Streptococcus agalactiae* is an important pathogen of fish and has been identified in farmed, wild, and ornamental species (Bowater, Forbes-Faulkner, Anderson, Condon, Robinson, Kong, Gilbert, Reynolds, Hyland, McPherson, Brien & Blyde 2012; Delannoy, Crumlish, Fontaine, Pollock, Foster, Dagleish, Turnbull & Zadoks 2013; Evans, Bohnsack, Klesius, Whiting, Garcia, Shoemaker & Takahashi 2008). Farmed fish affected by *S. agalactiae* include economically important species such as tilapia and ya fish (Delannoy et al. 2013; Geng, Wang, Huang, Chen, Li, Ren, Liao, Zhou, Liu, Du & Lai 2012; Mian, Godoy, Leal, Yuhara, Costa & Figueiredo 2009). Based on multilocus sequence typing (MLST), the main strains of *S. agalactiae* associated with fish are members of a limited number of clonal complexes (CC), i.e. CC7 and CC552 (Delannoy et al. 2013; Evans et al. 2008). Detection of CC7, which is beta-haemolytic, is largely limited to Asia, whereas CC552, which is non-haemolytic, has been reported worldwide and in a large number of fish species. Of the main CCs associated with fish, CC552 has been detected exclusively in poikilothermic species. The vast majority of CC552 isolates originate from fish (Delannoy et al., 2013; Evans et aL, 2008), with a few isolates from frogs described as non-haemolytic, serotype 1 b or ST260 belonging probably or certainly to CC552 (Amborski, Snider, Thune & Culley 1983; Elliott, Facklam & Richter 1990; Lopez-Sanchez, Sauvage, Da Cunha, Clermont, Ratsima Hariniaina, Gonzalez-Zorn, Poyart, Rosinski-Chupin & Glaser 2012). By contrast, CC7 has also been isolated from humans, where it has been associated with asymptomatic carriage in the genitourinary tract and with disease (Jones, Bohnsack, Takahashi, Oliver, Chan, Kunst, Glaser, Rusniok, Crook, Harding, Bisharat & Spratt 2003; Ip, Cheuk, Tsui, Kong, Leung & Gilbert 2006). Many other CCs have been linked to carriage or disease in people and in homeothermic animals, most importantly in cattle, including members of CC1, CC19 and CC23 (Manning, Springman, Lehotzky, Lewis, Whittam & Davies 2009; Zadoks, Middleton, McDougall, Katholm & Schukken 2011). However, none of these CCs have been reported in fish. CC23 is of particular interest because its host range is known to include aquatic mammals, such as seals, and poikilotherms, such as crocodiles (Bishop, Shilton, Benedict, Kong, Gilbert, Gal, Godoy, Spratt & Currie 2007; Delannoy, et al. 2013), yet it has never been identified in fish.

Indeed, challenge studies in tilapia using two serotypes of ST23 have demonstrated that this ST is non-virulent in fish (Delannoy C M, Zadoks R N, Crumlish M, Rodgers D, Lainson F A, Ferguson H W, Turnbull J, Fontaine M C. Genomic comparison of virulent and non-virulent *Streptococcus agalactiae* in fish. J Fish Dis. 2014 Nov. 15. doi: 10.1111/jfd.12319 and Mian G F, Godoy D T, Leal C A, Yuhara T Y, Costa G M, Figueiredo H C. Aspects of the natural history and virulence of *S. agalactiae* infection in Nile tilapia. Vet Microbiol. 2009 Apr. 14; 136(1-2):180-3. doi: 10.1016/j.vetmic.2008.10.016).

Comparative genomic analysis of *S. agalactiae* isolates with distinct clinical origins or host associations has provided insight into potential mechanisms of evolution, virulence and host adaptation. For example, hypervirulence of ST17 in human neonates has been linked to a specific adhesin (Tazi, Disson, Bellais, Bouaboud, Dmytruk, Dramsi, Mistou, Khun, Mechler, Tardieux, Trieu-Cuot, Lecuit & Poyart 2010), presence of the lactose operon has been linked to strains that affect milk production in dairy cattle (Richards, Lang, Pavinski Bitar, Lefébure, Schukken, Zadoks & Stanhope 2011) and reductive evolution has been suggested as contributing to niche restriction of ST260 (Rosinski-Chupin, Sauvage, Mairey, Mangenot, Ma, Da Cunha, Rusniok, Bouchier, Barbe & Glaser 2013). Genomic comparison of piscine, human and bovine strains of *S. agalactiae* has thus far failed to identify specific genes required for virulence in fish (Liu, Zhang & Lu 2013).

SUMMARY OF THE INVENTION

The present invention is based upon the identification of a number of *Streptococcus agalactiae* genes which are conserved among disease-causing strains and hence are likely to contribute to virulence and hence make good targets for the development of vaccines and diagnostic tests. Specifically, the invention relates to genomic content present in fish-associated *S. agalactiae* strains that is absent from strains which are non-virulent to fish.

By analyzing the genomic content of *S. agalactiae* strains known to be virulent in fish and comparing the information obtained with genomic information derived from *S. agalactiae* strains known not to be virulent in fish, the inventors have been able to identify a number of fish-specific/associated genes. Moreover, the inventors have been able to show that these fish-specific/associated genes, are distributed over a number of small clusters or loci.

Given that the identified genes are present only in *S. agalactiae* strains known to be virulent in fish, it is suggested that these genes and/or their products facilitate virulence in fish and/or contribute to fitness in the aquatic environment.

Specifically, the present invention relates to the *S. agalactiae* genes identified in Table 1.

TABLE 1

Candidate fish-specific and fish associated genes identified in the genome of *Streptococcus agalactiae* STIR-Cd-17. Genes were considered as fish-specific if they were identified in the genome of CC552 isolates on and as fish-associated if they were identified in the genomes of CC552 and CC7 isolates but not in the genomes of isolates from other clonal complexes (CC).

| Locus tag | NCBI annotation | | | Generator analysis | BlastP results based on NCBI search | | |
|---|---|---|---|---|---|---|---|
| | Bp | Putative function and COG | PSORTb | | Species and strains | Product | BSR |
| | | | | | LOCUS 1 (Contig23) | | |
| M3M_05402 | 801 | hypothetical protein | C | — | *S. agalactiae* SA20-06 | hypothetical protein SaSA20_0045 | 1 |
| | | | | | *Eremococcus coleocola* ACS-139-V-Col8 | oxidoreductase, NAD-binding domain protein | 0.072 |
| | | | | | *Tribolium castaneum* | hypothetical protein TcasGA2_TC008151 | 0.069 |
| M3M_05407 | 591 | hypothetical protein | C | — | *S. agalactiae* SA20-06 | hypothetical protein SaSA20_004 | 1 |
| | | | | | *S. oralis* SK304 | hypothetical protein HMPREF1125_1048 | 0.166 |
| | | | | | *Campylobacter jejuni* subsp. *jejuni* BH-01-0142 | hypothetical protein CJBH_0152c | 0.096 |
| | | | | | LOCUS 2 (Contig753) | | |
| M3M_01252 | 222 | hypothetical protein | C | — | *S. agalactiae* SA20-06 | hypothetical protein gbs0229 | 1 |
| | | | | | *S. agalactiae* 515/NEM316 | Unknown | 0.623 |
| | | | | | *S. agalactiae* ATCC 13813 | hypothetical protein HMPREF9171_2185 | 0.617 |
| | | | | | LOCUS 3 (Contig753) | | |
| M3M_01147 | 195 | aldose 1-epimerase, interruption-C (galM); COG2017 Galactose mutarotase and related enzymes | U | A909, H36B | *S. agalactiae* SA20-06 | aldose 1-epimerase | 1 |
| | | | | | *S. agalactiae* A909 | hypothetical protein SAK_0542 | 0.993 |
| | | | | | *S. agalactiae* H36B | aldose 1-epimerase | 0.993 |
| | | | | | *S. agalactiae* GD201008-001/ZQ0910 | hypothetical protein | 0.993 |
| | | | | | *Streptococcus suis* ST3 | galactose mutarotase-like protein | |
| M3M_01152 | 564 | aldose 1-epimerase, interruption-N (galM); COG2017 Galactose mutarotase and related enzymes | C | A909, H36B | *S. agalactiae* SA20-06 | aldose 1-epimerase | 1 |
| | | | | | *S. agalactiae* A909 | hypothetical protein SAK_0539 | 0.966 |
| | | | | | *S. agalactiae* H36B | aldose 1-epimerase, interruption-N | 0.966 |
| | | | | | *S. agalactiae* GD201008-001/ZQ0910 | hypothetical protein | 0.964 |
| | | | | | *Streptococcus suis* ST3 | galactose mutarotase-like protein | 0.606 |
| M3M_01157 | 996 | UDP-glucose 4-epimerase (galE1); COG1087 UDP-glucose 4-epimerase | U | A909, H36B | *S. agalactiae* SA20-06 | UDP-glucose 4-epimerase | 0.999 |
| | | | | | *S. agalactiae* A909/h36b/GD201008-001/ZQ0910 | UDP-glucose 4-epimerase | 0.993 |
| | | | | | *S. gallolyticus* UCN34 | UDP-glucose 4-epimerase | 0.834 |
| M3M_01162 | 1482 | galactose-1-phosphate uridylyltransferase (galT); COG4468 Galactose-1-phosphate uridylyltransferase | C | A909, H36B | *S. agalactiae* SA20-06 | galactose-1-phosphate uridylyltransferase | 0.996 |
| | | | | | *S. agalactiae* H36B | galactose-1-phosphate uridylyltransferase | 0.991 |
| | | | | | *S. agalactiae* G0201008-001 | galactose-1-phosphate uridylyltransferase | 0.989 |
| | | | | | *S. agalactiae* A909/ZQ0910 | galactose-1-phosphate uridylyltransferase | 0.988 |
| | | | | | *S. sanguinis* SK355 | UTP-hexose-1-phosphate uridylyltransferase | 0.693 |
| M3M_01167 | 1173 | galactokinase (galK); COG0153 Galactokinase | C | H36B | *S. agalactiae* H36B | galactokinase | 0.914 |
| | | | | | *S. agalactiae* SA20-06 | galactokinase | 0.909 |
| | | | | | *S. gallolyticus* subsp. *gallolyticus* TX20005 | galactokinase | 0.771 |
| M3M_01172 | 2202 | alpha-galactosidase (galA); COG3345 Alpha-galactosidase | C | A909, H36B | *S. agalactiae* SA20-06 | alpha-galactosidase | 0.999 |
| | | | | | *S. agalactiae* A909/GD201008-001/ZQ0910/H36B | alpha-galactosidase | 0.993 |
| | | | | | *S. canis* FSL Z3-227 | alpha-galactosidase | 0.692 |

TABLE 1-continued

Candidate fish-specific and fish associated genes identified in the genome of *Streptococcus agalactiae* STIR-Cd-17. Genes were considered as fish-specific if they were identified in the genomes of CC552 isolates on and as fish-associated if the were identified in the genomes of CC552 and CC7 isolates but not in the genomes of isolates from other clonal complexes (CC).

| | NCBI annotation | | | Generator | BlastP results based on NCBI search | | |
|---|---|---|---|---|---|---|---|
| Locus tag | Bp | Putative function and COG | PSORBTb | analysis | Species and strains | Product | BSR |
| M3M_01177 | 828 | ABC transporter permease; COG0395 ABC-type sugar transport system, permease component | CM | A909, H36B | *S. agalactiae* SA20-06<br>*S. agalactiae* A909/GD201008-001/ZQ0910/H36B<br>*S. canis* FSL Z3-227 | ABC transporter permease<br>ABC transporter permease<br>ABC transporter permease | 1<br>1<br>0.873 |
| M3M_01182 | 903 | sugar ABC transporter permease; COG1175 ABC-type sugar transport systems, permease components | CM | A909, H36B | *S. agalactiae* SA20-06<br><br>*S. agalactiae* A909/GD201008-001/ZQ0910/H36B<br>*S. canis* FSL Z3-227<br>*S. iniae* 9117 | binding-protein-dependent transport system<br>sugar ABC transporter permease<br>ABC-type sugar transport system, permease component<br>ABC superfamily ATP binding cassette transporter | 0.997<br>0.931<br>0.815<br>0.794 |
| M3M_01187 | 1035 | sugar ABC transporter sugar-binding protein; COG1653 ABC-type sugar transport system, periplasmic component | U | A909, H36B | *Streptococcus agalactiae* SA20-06<br>*S. agalactiae* A909/GD201008-001/ZQ0910/H36B<br>*Streptococcus porcinus* str. Jelinkova 176 | sugar ABC transporter substrate-binding protein<br>sugar ABC transporter sugar-binding protein<br>ABC transporter, solute-binding protein | 0.993<br>0.742<br>0.574 |
| M3M_01192 | 831 | AraC family transcriptional regulator; COG2207 AraC-type DNA-binding domain-containing proteins | C | A909, H36B | *S. agalactiae* A909/GD201008-001/ZQ0910/H36B/SA20-06<br>*S. canis* FSL Z3-227<br>*S. suis* 05ZYH33 | AraC family transcriptional regulator<br>transcriptional regulator<br>transcriptional regulator | 1<br>0.655<br>0.652 |
| M3M_01197 | 285 | phosphotransferase system, galactitol-specific IIB component; COG3414 Phosphotransferase system, galactitol-specific IIB component | CM | A909, H36B | *S. agalactiae* SA20-06<br>*S. agalactiae* A909/GD201008-001/ZQ0910/H36B<br>*S. ictaluri* 707-05<br>*S. pseudoporcinus* SPIN 20026 | PTS system lactose/cellobiose specific transporter<br>PTS system galactitol-specific transporter subunit IIB<br>PTS system, Lactose/Cellobiose specific IIB subunit<br>putative PTS system, galactitol-specific IIB component | 1<br>0.989<br>0.832 |
| M3M_01202 | 1332 | PTS system, galactitol-specific IIC component; COG3775 Phosphotransferase system, galactitol-specific IIC component | CM | A909, H36B | *S. agalactiae* A909/GD201008-001/ZQ0910/H36B<br>*S. agalactiae* SA20-06<br>*Granulicatella adiacens* ATCC 49175<br>*S. iniae* 9117 | PTS system galactitol-specific transporter subunit IIC<br>PTS system component<br>PTS system, galactitol-specific IIC component<br>PTS family galactitol (gat) porter component IIC | 0.821<br>0.995<br>0.923<br>0.831<br>0.811 |
| M3M_01207 | 465 | PTS system, galactitol-specific IIA component; COG1762 Phosphotransferase system mannitol/fructose-specific IIA domain | C | A909, H36B | *S. agalactiae* SA20-06<br>*S. agalactiae* A909/GD201008-001/ZQ0910/H36B | PTS system galactitol-specific transporter subunit IIA<br>PTS system, galactitol-specific IIA component, putative | 0.99<br>0.977 |
| M3M_01212 | 831 | rhamnulose-1-phosphate aldolase; COG0235 Ribulose-5-phosphate 4-epimerase and related epimerases and aldolases | C | A909, H36B | *Granulicatella elegans* ATCC 700633<br>*S. agalactiae* A909/GD201008-001/ZQ0910/H36B<br>*S. agalactiae* SA20-06<br>*S. anginosus* subsp. *whileyi* CCUG 39159 | PTS system IIA component<br>rhamnulose-1-phosphate aldolase<br>rhamnulose-1-phosphate aldolase<br>putative rhamnulose-1-phosphate aldolase | 0.451<br>0.997<br>0.995<br>0.705 |

TABLE 1-continued

Candidate fish-specific and fish associated genes identified in the genome of *Streptococcus agalactiae* STIR-Cd-17. Genes were considered as fish-specific if they were identified in genomes of CC552 isolates on and as fish-associated if they were identified in the genomes of CC552 and CC7 isolates but not in the genomes of isolates from other clonal complexes (CC).

| | NCBI annotation | | | Generator analysis | BlastP results based on NCBI search | | |
|---|---|---|---|---|---|---|---|
| Locus tag | Bp | Putative function and COG | PSORBTb | | Species and strains | Product | BSR |
| M3M_01217 | 1338 | PTS system, galactitol-specific IIC component; COG3775 Phosphotransferase system, galactitol-specific IIC component | CM | A909, H36B | S. agalactiae SA20-06<br>S. agalactiae A909/GD201008-001/Z00910<br>S. anginosus subsp. whileyi CCUG 39159 | PTS system sugar-specific transporter permease<br>PTS system galactitol-specific transporter subunit IIC<br>PTS system sugar-specific permease protein | 1<br>0.995<br>0.905 |
| M3M_01222 | 279 | PTS system galactitol-specific enzyme IIB component; COG3414 Phosphotransferase system, galactitol-specific IIB component | U | A909, H36B | S. agalactiae SA20-06<br>S. agalactiae A909/GD201008-001/ZQ0910/H36B<br>S. anginosus subsp. whileyi CCUG 39159<br>Granulicatella elegans ATCC 700634<br>Streptococcus ictaluri 707-05 | PTS system lactose/cellobiose specific transporter<br>PTS system galactitol-specific transporter subunit IIB<br>PTS system, lactose/cellobiose-specific IIB subunit<br>PTS system galactitol-specific transporter subunit IIB<br>PTS system, Lactose/Cellobiose specific IIB subunit | 1<br>0.984<br>0.886<br>0.864<br>0.842 |
| M3M_01227 | 450 | PTS system, galactitol-specific IIA component; COG1762 Phosphotransferase system mannitol/fructose-specific IIA domain | C | A909, H36B | S. agalactiae A909/GD201008-001/ZQ0910/H36B/SA20-06<br>S. porcinus str. Jelinkova 176<br>S. anginosus subsp. whileyi CCUG 39159 | PTS system galactitol-specific transporter subunit IIA<br>phosphoenolpyruvate-dependent sugar PTS family porter<br>phosphoenolpyruvate-dependent sugar PTS family porter | 1<br>0.219<br>0.217 |
| M3M_01232 | 2043 | PTS system IIA domain-containing protein; COG3711 Transcriptional antiterminator | C | A909, H36B | S. agalactiae SA20-06<br>S. agalactiae ZQ0910<br>S. agalactiae A909/GD201008-001<br>S. agalactiae H36B<br>Coprobacillus sp. 29_1<br>LOCUS 4<br>(Contig753) | hypothetical protein SaSA20_0403<br>PTS system IIA domain-containing protein<br>PTS system IIA domain-containing protein<br>MW0309, putative<br>hypothetical protein HMPREF9488_00517 | 0.999<br>0.996<br>0.996<br>0.986<br>0.247 |
| M3M_01047 | 294 | hypothetical protein; COG1343 Uncharacterized protein predicted to be involved in DNA repair csd1 pseudogene | C | — | S. agalactiae SA20-06<br>S. constellatus subsp. constellatus SK53<br>S. mutans UA159 | CRISPR-associated endoribonuclease Cas2<br>CRISPR-associated endoribonuclease Cas2<br>hypothetical protein SMU_1753c | 1<br>0.945<br>0.935 |
| M3M_01062 | 672 | putative RecB family exonuclease; COG1468 RecB family exonuclease | C | — | S. agalactiae SA20-06<br>S. mutans LJ23<br>S. mutans UA159 | CRISPR-associated protein Cas4<br>CRISPR-associated protein cas4<br>hypothetical protein | 1<br>0.879<br>0.864 |
| M3M_01068 | 850 | hypothetical protein; COG3649 Uncharacterized protein predicted to be involved in DNA repair | C | — | S. agalactiae SA20-06<br>S. dysgalactiae subsp. equisimilis RE378<br>S. dysgalactiae subsp. equisimilis SK1251 | Csd2 family CRISPR-associated protein<br>putative cytoplasmic protein<br>hypothetical protein HMPREF9963_1905 | 1<br>0.981<br>0.979 |
| M3M_01097 | 729 | hypothetical protein | C | 515 | S. agalactiae SA20-06<br>S. dysgalactiae subsp. equisimilis AC-2713<br>S. canis FSL Z3-227 | CRISPR-associated protein Cas5<br>hypothetical protein SDSE_1670<br>hypothetical protein SCAZ3_08370 | 1<br>0.964<br>0.962 |

TABLE 1-continued

Candidate fish-specific and fish associated genes identified in the genome of *Streptococcus agalactiae* STIR-Cd-17. Genes were considered as fish-specific if they were identified in genomes of CC552 isolates on and as fish-associated if they were identified in the genomes of CC552 and CC7 isolates but not in the genomes of isolates from other clonal complexes (CC).

| Locus tag | NCBI annotation | | PSORTBb | Generator analysis | BlastP results based on NCBI search | | BSR |
| | Bp | Putative function and COG | | | Species and strains | Product | |
|---|---|---|---|---|---|---|---|
| M3M_01102 | 2424 | ATP-dependent RNA helicase; COG1203 Predicted helicases | C | 515, COH1, FSL-S3-026 | S. agalactiae SA20-06<br>S. dysgalactiae subsp. equisimilis SK1250<br>S. dysgalactiae subsp. equisimilis AC-2713 | CRISPR-associated helicase Cas3<br>CRISPR-associated helicase Cas3<br>Pre-mRNA-processing ATP-dependent RNA helicase PRP5 | 0.997<br>0.956<br>0.953 |
| M3M_01107 | 222 | Fic protein family; COG2184 Protein involved in cell division | U | 515 | S. agalactiae 515<br>S. suis 05ZYH33<br>S. suis ST1<br>LOCUS 5 (Contig751) | Fic protein family family<br>hypothetical protein SSU05_0462<br>hypothetical protein SSUST1_0463 | 0.968<br>0.613<br>0.613 |
| misc_feature | — | CHAP domain protein | — | — | — | — | — |
| misc_feature | — | — | — | — | — | — | — |
| misc_feature | — | resolvase family site-specific recombinase | — | — | — | — | — |
| misc_feature | — | resolvase family site-specific recombinase | — | — | — | — | — |
| M3M_00445 | 204 | bacteriocin | E | — | S. agalactiae SA20-06<br>S. equi subsp. zooepidemicus MGCS10565<br>S. equi subsp. equi<br>S. agalactiae SA20-06<br>S. pneumoniae SP6-BS73<br>S. equi subsp. equi 4047 | hypothetical protein SaSA20_0545<br>bacteriocin BlpN-like<br>Streptococcus equi subsp. equi 404<br>hypothetical protein SaSA20_0544<br>bacteriocin BlpM<br>bacteriocin | 1<br>0.576<br>0.57<br>1<br>0.687<br>0.649 |
| M3M_00450 | 231 | hypothetical protein | U | — | — | — | — |
| misc_feature | — | abortive infection protein AbiGII | — | — | — | — | — |
| M3M_00465 | 582 | hypothetical protein; COG1672 Predicted ATPase (AAA+ superfamily) | C | — | S. agalactiae SA20-06<br>S. macedonicus ACA-DC 198<br>S. dysgalactiae subsp. dysgalactiae ATCC 27957 | hypothetical protein SaSA20_0542<br>Abortive infection protein AbiGI<br>hypothetical protein SDD27957_04365 | 1<br>0.691<br>0.686 |
| M3M_00470 | 138 | Tn5252 Orf28; COG3942 Surface antigen | U | — | S. agalactiae SA20-06<br>S. intermedius F0395<br>S. suis D12 | hypothetical protein SaSA20_0541<br>hypothetical protein HMPREF9682_00655<br>hypothetical protein SSUD12_0897 | 0.971<br>0.869<br>0.783 |
| M3M_00475 | 327 | hypothetical protein; COG0270 Site-specific DNA methylase | C | — | S. agalactiae SA20-06<br>S. agalactiae NEM316<br>S. pneumoniae NorthCarolina6A-23<br>LOCUS 6 (Contig751) | hypothetical protein SaSA20_0540<br>hypothetical protein<br>modification methylase HpaII | 1<br>0.371<br>0.357 |
| M3M_00390 | 270 | hypothetical protein | U | — | Ashbya gossypii<br>delta proteobacterium<br>Photorhabdus asymbiotica | AAR1442Cp<br>Response regulator receiver<br>Gramicidin S synthetase 2 | 0.192<br>0.192<br>0.187 |
| M3M_00395 | 897 | hypothetical protein | C | — | Krokinobacter sp. | hypothetical protein | 0.06 |

TABLE 1-continued

Candidate fish-specific and fish associated genes identified in the genome of *Streptococcus agalactiae* STIR-Cd-17. Genes were considered as fish-specific if they were identified in genomes of CC552 isolates on and as fish-associated if they were identified in the genomes of CC552 and CC7 isolates but not in the genomes of isolates from other clonal complexes (CC).

| Locus tag | NCBI annotation | | | Generator analysis | BlastP results based on NCBI search | | |
|---|---|---|---|---|---|---|---|
| | Bp | Putative function and COG | PSORTb | | Species and strains | Product | BSR |
| M3M_00400 | 1017 | hypothetical protein; COG0457 FOG: TPR repeat | C | — | *Gloeobacter violaceus*<br>*Helicobacter pylori* F32 | hypothetical protein<br>hypothetical protein HPF32_0454 | 0.057<br>0.052 |
| M3M_00405 | 1263 | serine hydroxymethyltransferase; COG0112 Glycine/serine hydroxymethyltransferase | C | — | *Fusobacterium* sp.<br>*Coprococcus eutactus* ATCC 27759 | conserved hypothetical protein<br>hypothetical protein COPEUT_02118 | 0.321<br>0.293 |
| M3M_00410 | 318 | integrase; COG4974 Site-specific recombinase XerD | U | — | *Erysipelotrichaceae* bacterium 3_1_53<br>*Streptococcus porcinus* str. Jelinkova 176<br>*Streptococcus anginosus* subsp. *whileyi* CCUG 39159<br>*Streptococcus mitis* by. 2 str. SK95 LOCUS 7 (Contig371) | hypothetical protein HMPREF0983_03234<br>phage integrase, N-terminal SAM domain protein<br>site-specific recombinase, phage integrase family<br>phage integrase, N-terminal SAM domain protein | 0.246<br>0.73<br>0.707<br>0.66 |
| M3M_04250 | 357 | integrase; COG0582 Integrase | U | — | *S. agalactiae* SA20-06<br>*S. pneumoniae* 70585<br>*S. pneumoniae* 2061617 | hypothetical protein SaSA20_0928<br>Integrase<br>phage integrase family protein | 0.992<br>0.633<br>0.633 |
| M3M_04255 | 189 | hypothetical protein | U | — | *S. agalactiae* SA20-06<br>*S. pneumoniae* GA47461<br>*S. pneumoniae* GA17484 | hypothetical protein SaSA20_0927<br>hypothetical protein SPAR97_1602<br>hypothetical protein SPAR47_088 | 1<br>0.675<br>0.675 |
| M3M_04260 | 126 | Cro/C1 family transcriptional regulator | U | — | *S. agalactiae* SA20-06<br>*S. pneumoniae* CCRI 1974<br>*S. pneumoniae* CCRI 1974M2 | hypothetical protein SaSA20_0926<br>hypothetical protein SpneC1_02124<br>hypothetical protein SpneC19_10413 | 1<br>0.681<br>0.681 |
| M3M_04265 | 339 | hypothetical protein | U | — | *S. agalactiae* SA20-06<br>*Oenococcus oeni* AWRIB429<br>*Oenococcus oeni* AWRIB548 | hypothetical protein SaSA20_0925<br>hypothetical protein AWRIB429_1949<br>phage terminase large subunit | 0.693<br>0.155<br>0.155 |
| M3M_04270 | 792 | hypothetical protein | U | — | *Bacillus amyloliquefaciens* DC-12<br>*Bacillus* sp. 5B6<br>*Bacillus amyloliquefaciens* AS43.3 | hypothetical protein BanyaD_16251<br>hypothetical protein MY7_0533<br>hypothetical protein B938_03325 | 0.137<br>0.135<br>0.129 |

TABLE 1-continued

Candidate fish-specific and fish associated genes identified in the genome of *Streptococcus agalactiae* STIR-Cd-17. Genes were considered as fish-specific if they were identified in genomes of CC552 isolates on and as fish-associated if they were identified in the genomes of CC552 and CC7 isolates but not in the genomes of isolates from other clonal complexes (CC).

| Locus tag | NCBI annotation | | | Generator analysis | BlastP results based on NCBI search | | |
|---|---|---|---|---|---|---|---|
| | Bp | Putative function and COG | PSORTBb | | Species and strains | Product | BSR |
| M3M_04275 | 639 | hypothetical protein; COG0477 Permeases of the major facilitator superfamily | CM | — | *Clostridiales* bacterium OBRC5-5<br>*Lachnospiraceae* oral taxon 107 str. F0167<br>*Staphylococcus hominis* SK119 | hypothetical protein HMPREF1135_01905<br>hypothetical protein HMPREF0491_01439<br>multidrug resistance protein 1 | 0.402<br>0.368<br>0.114 |
| M3M_04280 | 369 | beta-hydroxyacyl-(acyl-carrier-protein) dehydratase FabA/FabZ; COG0764 3-hydroxymyristoyl/3-hydroxydecanoyl-dehydratases | U | — | *Geobacillus thermoleovorans* CCB_US3_UF5<br>*Coraliomargarita akajimensis* DSM 45221<br>*Pirellula staleyi* DSM 6068 | putative thioester dehydrase<br>beta-hydroxyacyl-dehydratase FabA/FabZ<br>beta-hydroxyacyl- dehydratase FabA/FabZ | 0.311<br>0.292<br>0.289 |
| M3M_04285 | 540 | PadR family transcriptional regulator COG1695 Predicted transcriptional regulators | C | — | *S. agalactiae* SA20-06<br>*Lachnospiraceae* oral taxon 107 str. F0167<br>*Clostridiales* bacterium OBRC5-5 | hypothetical protein SaSA20_0923<br>hypothetical protein HMPREF0491_01453<br>hypothetical protein HMPREF1135_01904 | 1<br>0.255<br>0.254 |
| | | | | | LOCUS 8 (Contig381) | | |
| M3M_01921 | 618 | DJ-1/PfpI family protein; COG0693 Putative intracellular protease/amidase | U | — | *S. agalactiae* SA20-06<br>*S. criceti* HS-6 | hypothetical protein SaSA20_1488<br>hypothetical protein STRCR_0670 | 1<br>0.761 |
| M3M_01926 | 531 | hypothetical protein; COG3797 Uncharacterized protein conserved in bacteria | C | — | *S. sanguinis* SK1087<br>*S. agalactiae* SA20-06<br>*S. suis* ST1<br>*S. suis* R61 | ThiJ/PfpI family intracellular protease<br>*Streptococcus agalactiae* SA20-06<br>hypothetical protein SSUST1_1897<br>hypothetical protein SSUR61_0033 | 0.613<br>1<br>0.725<br>0.706 |

As noted in Table 1 above, the candidate genes which are the subject of this invention have been identified as belonging to a number of distinct clusters—referred to herein as "loci". The Table shows that the inventors have identified 8 loci.

While the invention relates to each of the genes identified in Table 1, it further relates to proteins and peptides (the gene "products") encoded by the same.

For convenience and simplicity, the genes identified in Table 1 and their peptide/protein products, shall be referred to hereinafter as "fish-associated sequences".

It should be understood that the term "fish-associated sequences" encompasses not only all of the genes and gene products identified in Table 1 but also the homologous/identical sequences, fragments, fusions, derivatives, variants antigens and the like described in more detail below.

In addition to the specific fish-associated sequences identified in Table 1, this invention may relate to similar or homologous sequences from other streptococci or S. agalactiae strains. Similar or homologous sequences within the scope of this invention may share some identity and/or homology to or with the nucleic acid and/or amino acid sequences of the genes and/or their protein products identified in Table 1. For example, homologous or identical sequences (both nucleic acid and/or amino acid) which are to be considered as encompassed within the scope of this invention may include those that exhibit at least about 60% to about 99% sequence identity to the nucleic acid or amino acid sequences of the genes and proteins identified in Table 1. For example homologous or identical sequences (both nucleic acid and amino acid) may exhibit at least about 65%, 70%, 75%, 80%, 85%, 90%, 91%, 92%, 93%, 94%, 95%, 96%, 97% or 98% identity or homology to the nucleic acid or amino acid sequences of the genes and proteins identified in Table 1.

The various genes and their protein products identified in Table 1 may be referred to as reference (fish-associated) sequences. Thus, homologous or identical sequences within the scope of this invention embraces those exhibiting homology or identity (as defined above) to the reference sequences disclosed herein.

The degree of (or percentage) "homology" between two or more (amino acid or nucleic acid) sequences may be determined by aligning the sequences and determining the number of aligned residues which are identical or which are not identical but which differ by redundant nucleotide substitutions (the redundant nucleotide substitution having no effect upon the amino acid encoded by a particular codon, or conservative amino acid substitutions).

A degree (or percentage) "identity" between two or more (amino acid or nucleic acid) sequences may also be determined by aligning the sequences and ascertaining the number of exact residue matches between the aligned sequences and dividing this number by the number of total residues compared—multiplying the resultant figure by 100 would yield the percentage identity between the sequences.

In addition, the invention may concern fragments of any of the fish-associated sequences disclosed herein. A fragment of a nucleic acid or amino acid sequence (including those described herein) may comprise, consist or consist essentially of from about 5, 10, 15, 20, 25, 30, 35, 40, 45 or 50 (amino acid or nucleic acid) residues to n−1 residues, where "n" is the total number of (amino acid or nucleic acid) residues in the relevant complete or native sequence. For the avoidance of doubt, the complete or native sequence may be any of the reference (fish-associated) sequences to which this invention relates.

The fragments of this invention may be functional fragments—that is to say the fragment retains one or more functional properties of the native or complete gene or protein sequence from which it is derived. Additionally or alternatively, the fragments of this invention may be antigenically and/or immunologically similar or identical to the native or complete gene/protein sequence (for example any of the sequences identified in Table 1) from which they are derived.

Fragments of any of the fish-associated sequences of this invention may comprise a number of contiguous or consecutive residues of a complete sequence. Fragments may alternatively or additionally comprise or consist (essentially) of, one or more domains and/or sequences of discontinuous residues from any of the complete fish-associated sequences of this invention.

The invention also relates to oligonucleotide and/or peptide probes and/or primers with specificity for any part of the fish-associated sequences described herein. For example the oligonucleotide and/or protein probes or primers of this invention may comprise sequences which are complementary to all or part of the sequence of a fish-associated sequence of this invention. Oligonucleotide primers may be used in PCR based methods or isothermal amplification procedures to amplify nucleic acid sequences of interest and therefore primers of this invention (which are complementary to sequences of the fish-associated sequences of this invention) may be exploited in order to facilitate the amplification of all or part of the fish-associated sequences or in methods of detecting the same. Such methods may find application in the detection or identification of Streptococci which are pathogenic to fish.

The probes/primers of this invention may be labeled with optically detectable tags and/or mass tags or the like. Optically detectable tags may include fluorescent tags such as fluorophores and the like. For example, the probes/primers of this invention may be labeled with cyanine, fluorescein, rhodamine, Alexa Fluors, Dylight fluors, ATTO Dyes, BODIPY Dyes, SETA Dyes and SeTau Dyes. The probes and/or primers may be modified so as to comprise sequences designed to create restriction sites in amplified sequences.

The invention may further relate to variants, derivatives or mutants of any of the fish-associated sequences described herein. One of skill will appreciate that a variant, derivative or mutant sequence may comprise or be encoded by, a nucleic acid or amino acid sequence which itself comprises one or more nucleotide and/or amino acid substitutions, inversions, additions and/or deletions relative to a reference sequence. As stated, in the context of this invention, a reference sequence may be any of the fish-associated sequences disclosed in Table 1. The term "substitution" may encompass one or more conservative substitution(s). The term "conservative substitution" is intended to embrace the act of replacing one or more amino acids of a protein or peptide with an alternate amino acid with similar properties and which does not substantially alter the physico-chemical properties and/or structure or function of the native (or wild-type) protein.

Sequences which are to be regarded as derived from (or derivatives of) any of the fish-associated sequences described herein may comprise one or more modifications to the structure or sequence. For example, derivative fish-associated sequences may comprise one or more synthetic or artificial amino acid/nucleic acid sequences. As described elsewhere, derivative or modified fish-associated sequences of this invention may be recombinantly produced.

As is well known in the art, the degeneracy of the genetic code permits substitution of one or more bases in a codon without changing the primary amino acid sequence. Consequently, although this specification presents a number of specific fish-associated sequences, the degeneracy of the code may be exploited to yield variant fish-associated nucleic acid sequences. These variant nucleic acid sequences may encode proteins/peptides (or fragments thereof) detailed in Table 1, but may differ from wild-type or native sequences by one or more nucleic acid residues. As stated, these variant nucleic acid sequences may encode primary amino acid sequences which are substantially identical to the wild-type primary sequences of those (fish-associated) proteins described in Table 1.

The invention may further relate to sequences, for example nucleic acid sequences, which have been codon optimised, perhaps for expression in certain cellular (for example bacterial) systems. As such, the term "fish-associated sequences" encompasses codon-optimised nucleic acid sequences encoding any of the proteins/peptides described in Table 1.

The invention may exploit nucleic acid (for example oligonucleotide) and/or amino acid (protein/peptide) fusions comprising any of the fish-associated sequences described herein. A fusion may comprise a fish-associated sequence fused, conjugated, bound or otherwise associated to or with some heterologous (for example a non-fish-associated sequence) sequence or moiety. Where the fusion is a fusion protein, the fusion may comprise a fish-associated sequence and a heterologous sequence (for example a non-fish-associated sequence) fused (directly or indirectly via a linker moiety) thereto.

Fusions may be generated using, for example, the recombinant (cloning and PCR based) technologies described herein.

The fish-associated sequences (for example any of the proteins identified in Table 1 and/or disclosed herein) may be purified directly from the relevant *S. agalactiae* strains, cultures and/or cell wall preparations thereof. For example, cell lysis and/or centrifugation techniques may be used to harvest internal (cytoplasmic) proteins as well as cell surface proteins. Nucleic acids may be extracted from cells by a number of known techniques including those which exploit the use of PCR and cloning procedures, silica-based nucleic acid extraction techniques (mini-spin columns and the like) and agarose gel extraction protocols.

The invention provides recombinant or synthetic forms of any of the fish-associated sequences described herein. Recombinant sequences (both nucleic acid and/or protein) may be produced by any number of well-known methods including those using PCR, cloning and protein/nucleic acid purification techniques.

Recombinant fish-associated sequences may be modified (relative to the corresponding wild-type sequence) to include synthetic (nucleic acid or amino acid) residues and/or sequences encoding tagging or labelling moieties. Additionally or alternatively, the recombinant fish-associated sequences may lack certain wild-type sequences or domains such as, for example, secretion signal peptide domains and the like.

One of skill in this field will appreciate that PCR techniques may be exploited to selectively amplify the appropriate gene sequences from a variety of sources including, for example, stored *S. agalactiae* isolates, clinical isolates, diseased (tissue) material and the like. Cloned fish-associated sequences of this invention may be introduced into a vector (such as a plasmid or expression cassette). In one embodiment, the vector may further comprise a nucleotide sequence of a tag or label to assist in protein purification procedures. The vector may encode a heterologous (relative to the fish-associated sequence) sequence which is to be fused to a fish-associated sequence of this invention.

A cell may be transformed or transfected with a vector of this invention—such cells may be referred to as "host cells". As such, the invention provides transformed/transfected host cells. A transformed/transfected cell may be maintained under conditions suitable to induce expression of any fish-associated sequence encoded by the vector. Prokaryotic or eukaryotic cells, such as, for example bacterial, plant, insect, mammalian and/or fungal cells, may be transformed or transfected with one or more of the vectors described herein. One of skill in this field will be familiar with the techniques used to introduce heterologous or foreign nucleic acid sequences, such as expression vectors, into cells, and these may include, for example, heat-shock treatment, use of one or more chemicals (such as calcium phosphate) to induce transformation/transfection, the use of viral carriers, microinjection and/or techniques such as electroporation. Further information regarding transformation/transfection techniques may be found in Current Protocols in Molecular Biology, Ausuble, F. M., ea., John Wiley & Sons, N.Y. (1989) which is incorporated herein by reference. In one embodiment, the host cell is a bacterial cell such as, for example, an *Escherichia coli* cell.

Techniques used to purify recombinant proteins generated in this way are known and, where the recombinant protein is tagged or labelled, these may include the use of, for example, affinity chromatography techniques.

In view of the above, this invention may provide or relate to expression vectors comprising one or more of the fish-associated (*S. agalactiae*) gene sequences and host cells transformed therewith. As a reminder, it should be understood that the term "fish-associated sequences" as used herein, encompasses all of the fragments, variants, homologous/identical and derivative sequences described herein.

The fish-associated sequences of this invention may find application in a variety of compositions, methods and procedures.

For example, the fish-associated sequences disclosed herein may be regarded as markers which indicate the ability of certain *Streptococcus* species or strains, for example strains of *S. agalactiae*, to cause disease in fish. As such, one or more of the fish-associated sequences of this invention may form the basis of tests to detect or identify *S. agalactiae* strains which have the potential to cause disease or be pathogenic in fish.

Thus, in a first aspect, the invention provides a method of screening for or detecting or identifying streptococci which are pathogenic in fish, said method providing a strain or species of *Streptococcus* to be tested and detecting the expression and/or presence of one or more of the genes and/or proteins identified in Table 1, wherein detection of the expression and/or presence of one or more of the genes and/or proteins identified in Table 1 indicates that the *Streptococcus* is a *Streptococcus* which is pathogenic in fish.

For example, the invention may exploit one or more of the genes contained within one or more of loci 1-8 identified in Table 1 above. The invention may further exploit one or more genes encoding components of pathways which have now been associated with virulence in fish. For example, the invention may exploit one or more of the genes of locus 3 and/or one or more genes encoding components of the Leloir pathway. The invention may exploit one or more genes encoding one or more of the following proteins/enzymes/pathway components:

(i) Alpha-galactosidase;
(ii) rhamnulose-1-phosphate aldolase;
(iii) aldose 1-epimerase;
(iv) galactose mutarotase;
(v) galactokinase;
(vi) D-galactose-1-phosphate uridyltransferase;
(vii) UDP-galactose 4-epimerase;
(viii) ABC transporter permease;
(ix) sugar ABC transporter permease;
(x) sugar ABC transporter sugar-binding protein;
(xi) AraC family transcriptional regulator;
(xii) phosphotransferase system, galactitol-specific IIB component;
(xiii) PTS system, galactitol-specific IIC component;
(xiv) PTS system, galactitol-specific IIA component;
(xv) PTS system, galactitol-specific IIC component;
(xvi) PTS system galactitol-specific enzyme IIB component;
(xvii) PTS system, galactitol-specific IIA component; and
(xviii) PTS system IIA domain-containing protein.

It should be understood that the term "pathogenic" embraces any *Streptococcus* species or strain which has the ability to infect and/or cause disease in fish. Thus, the methods disclosed herein may be used to detect or identify those streptococci which are most likely to cause disease in fish.

The methods may be further applied to screening samples for the presence or absence of streptococci that are pathogenic to fish. For example, samples may be probed for the presence of one or more of the genes or proteins identified in Table 1.

Samples which may be subject to the methods of this invention may include any sample of matter which could contain streptococci potentially pathogenic to fish. In particular, samples derived from matter to which fish are likely to be exposed may be tested using the methods of this invention. For example, the term "sample" may include biological samples such as, for example, tissue biopsies and/or samples of cells, secretion, scrapings fluids, blood and the like. For example, biopsies from fish may be screened and/or probed for the presence or absence of pathogenic streptococci. The term "samples" may also encompass samples of water, food and substrates such as soil, sand, water body (for example lake, loch, pond, stream, river, sea or ocean) bed substrates. A sample may be a sample of a material, product or substrate used in a tank or other vessel suitable for holding fish.

In view of the above, the present invention may find particular application in the field of fish farming and aquaculture where the fish-associated sequences of this invention may form the basis of protocols useful to screen for streptococci which may cause disease.

The methods of the first and second aspects of this invention may be immunological and/or molecular/amplification based methods. One of skill will appreciate that immunological methods may exploit binding agents, for example antibodies and the like, with affinity and/or specificity for (i.e. an ability to bind to) any of the fish-associated sequences (in particular the proteinaceous products) described herein. Suitable immunological techniques include, for example ELISA and other types of immunoassay. Amplification methods may comprise, for example, isothermal amplification procedures and/or LAMP (loop mediated amplification: an alternative to PCR) as a method to detect oligonucleotides.

PCR (or molecular) methods may exploit oligonucleotides capable of binding to or interacting with one or more of the fish-associated sequences disclosed herein. For example, the invention may provide methods which exploit oligonucleotide or peptide sequences complementary to a sequence of one or more of the fish-associated sequences of this invention. The complementary sequences of the oligonucleotides or peptides of this invention may span, for example, about 5, 10, 15, 20, 25, 30, 35, 40, 45 or about 50 residues of any of the fish-associated sequences of this invention.

In view of the above and in a third aspect, this invention provides antibodies, including polyclonal and/or monoclonal antibodies (or antigen binding fragments thereof) that bind (or have affinity or specificity for) any of the fish-associated sequences provided by this invention. Production and isolation of polyclonal/monoclonal antibodies specific for protein/peptide sequences is routine in the art, and further information can be found in, for example "Basic methods in Antibody production and characterisation" Howard & Bethell, 2000, Taylor & Francis Ltd. Such antibodies may be used in diagnostic procedures to, for example, detect or diagnose *S. agalactiae* infection/infestations in an animal (for example, fish) species, as well as for passive immunisation.

One of skill will appreciate that, where a method of this invention exploits an immunological technique, one or more of the fish-associated sequences (for example one or more of the proteins identified in Table 1) may be immobilised to a substrate and the immobilised moiety used to probe a sample for the presence of antibodies reactive thereto. After a suitable period of incubation between the immobilised moiety and the sample, the presence or absence of antibodies may be detected by means of a secondary binding agent (for example an antibody) optionally conjugated to a detectable component, with specificity for the relevant antibody. The presence of antibody in a sample may indicate the presence of a streptococcal strain which is pathogenic to fish.

Alternatively, binding agents (for example aptamers (oligonucleotide/peptide type aptamers)) or antibodies with specificity to one or more of the *S. agalactiae* antigens described herein may be immobilised onto a substrate. The substrate may then be used to probe a sample for the presence of one or more *S. agalactiae* antigens. After a suitable period of incubation between the sample and the immobilised antibody, the substrate may be contacted with a secondary binding agent or antibody with specificity for the relevant antigen. The secondary binding agent or antibody may be conjugated to a detectable moiety. Alternatively, the immobilised binding agent:antigen:binding agent complexes may be further probed with a tertiary binding agent or antibody capable of binding to the secondary binding agent. The tertiary binding agent may be conjugated to a detectable moiety.

Other immunological techniques, such as immunohistochemical staining, may exploit binding agents (for example antibodies/conjugated antibodies) with specificity for one or more of the *S. agalactiae* antigens described herein to detect the presence or absence of *S. agalactiae* or *S. agalactiae* antigens in a sample.

It should be noted that while traditional ELISA and/or molecular (for example PCR) based methods may be used to execute the various methods of this invention, other techniques exploiting nanotechnology, microfluidics, electrochemistry (changes in electrical conductivity that result from the binding of a target (eg streptococcal) sequence to an aptamer bound to a carbon nanotube) may also be useful. Molecular methods useful to detect the presence of *S. agalactiae* or antigens therefrom in a sample may exploit primer sequences which amplify sequences encoding one or more of the fish-associated sequences/antigens of this invention. These primers may be used to probe samples for the presence of *S. agalactiae* nucleic acid. Further information regarding these (PCR-based) techniques may be found in, for example, PCR Primer: A Laboratory Manual, Second Edition Edited by Carl W. Dieffenbach & Gabriela S. Dveksler: Cold Spring Harbour Laboratory Press and Molecular Cloning: A Laboratory Manual by Joseph Sambrook & David Russell: Cold Spring Harbour Laboratory Press. Further information on isothermal amplification methods may be found, for example, in Yan L, Zhou J, Zheng Y, Gamson A S, Roembke B T, Nakayama S, Sintim H O. Isothermal amplified detection of DNA and RNA. Mol Biosyst. 2014 May; 10(5):970-1003. doi: 10.1039/c3mb70304e.

The present invention also extends to kits comprising reagents and compositions suitable for diagnosing and/or detecting *S. agalactiae* infections. For example, depending on whether or not the kits are intended to be used to identify levels of *S. agalactiae* antigen or antibodies thereto in samples, the kits may comprise substrates having *S. agalactiae* antigens (for example any of those identified in Table 1 or any of the fish-associated sequences/antigens described herein) or agents capable of binding any of the fish-associated sequences to which this invention relates, bound thereto. In addition, the kits may comprise agents capable of binding fish-associated sequences (antibodies, aptamers and the like)—particularly where the kit is to be used to identify levels of *S. agalactiae* antigen in samples. In other embodiments, the kit may comprise agents capable of binding the *S. agalactiae* antigens, for example specifically raised polyclonal antibodies or monoclonal antibodies. Kits for use in detecting the presence or expression of genes encoding the fish-associated sequences may comprise one or more of the oligonucleotides/primers described herein. The kits may also comprise other reagents to facilitate, for example, sequencing and/or PCR or isothermal analysis. All kits described herein may further comprise instructions for use.

The invention further provides immunogenic compositions comprising one or more of the fish-associated sequences described herein. In particular, the invention provides immunogenic compositions comprising one or more of the fish-associated protein sequences identified in Table 1. These protein sequences (or for example, any variants, derivatives, homologous and/or immunogenic fragments thereof) may be antigenic (antigens) and capable of eliciting or raising immune responses in animals.

The immunogenic compositions of this invention may find application as vaccines and thus the invention further provides vaccines and vaccine compositions.

For convenience, those sequences disclosed in this specification which encode antigens useful in the compositions or vaccines of this invention shall be referred to as "fish-associated antigens". Thus the vaccines and vaccine/immunogenic compositions of this invention may comprise one or more of the fish-associated antigens of this invention (for example those described in Table 1). The fish-associated antigens may (in use) elicit a "protective" immune response. One of skill will appreciate that the precise nature of the response (humoral and/or cellular, for example) may depend on the formulation of the antigen, its route of administration, the presence or absence of adjuvant, and the type of adjuvant employed.

In a fourth aspect, the invention provides an immunogenic composition comprising one or more of the fish-associated antigens described herein.

In a fifth aspect, the invention provides a vaccine or vaccine composition comprising one or more of the fish-associated antigens described herein.

The compositions or vaccine of the fourth and fifth aspects of this invention may comprise excipients such as pharmaceutically acceptable and/or sterile excipients, carriers and/or diluents. Additionally, or alternatively, the compositions or vaccines of this invention may further comprise or be admixed with, another component or components, such as another polypeptide and/or an adjuvant. Additionally, or alternatively, vaccines or vaccine compositions provided by this invention may, for example, contain viral, fungal, bacterial or other parasite whole cells/particles and/or antigens used to control other diseases/infections or infestations. For example, the vaccine or vaccine composition may be included within a multivalent vaccine, which includes antigens against other piscine pathogens/diseases.

In addition to compositions and/or vaccines which comprise fish-associated antigens, the invention further provides immunogenic compositions and vaccines which comprise attenuated or killed strains of *S. agalactiae* which express or harbour one or more of the fish-associated sequences described herein. The attenuated or killed *S. agalactiae* strains may not express one or more of the fish associated sequences of this invention. For example, the genome of a *S. agalactiae* strain to be used as a vaccine may be modified so as to (i) lack one or more of the genes encoding one or more of the fish-associated sequences described herein and/or (ii) comprise one or more genes modified to prevent functional expression of one or more of the fish-associated sequences of this invention.

The vaccines of this invention may also take the form of DNA type vaccines (used in association with an appropriate delivery system, such as liposomes, microspheres, attenuated bacterial vectors and the like). A DNA vaccine for use in an invention of this type may comprise sequences encoding one or more of the fish-associated sequences of this invention.

In view of the above, a further aspect of this invention provides a composition, immunogenic composition or vaccine composition comprising one or more of the fish-associated antigens described herein, for use in raising an immune response in an animal. In one embodiment, the immune response is a protective response. A protective immune response may be a response which neutralizes, inhibits or prevents a *Streptococcus agalactiae* infection and/or a disease or condition caused thereby or associated therewith.

In a further embodiment, the animal may be any animal susceptible to infection by or with an *S. agalactiae* strain (for example a strain which is pathogenic in fish). For example, the animal may be a fish.

In a yet further aspect, the invention provides the use of one or more of the fish-associated antigens described herein for the manufacture of a medicament or vaccine for use in the treatment and/or prevention of a *Streptococcus agalactiae* infection and/or a disease or condition caused thereby or associated therewith.

Moreover, the invention may provide one or more compounds which modulate any aspect of the function, activity and/or expression of one or more of the fish-associated sequences of this invention. Such compounds may be collectively referred to as "modulator compounds". For example, the modulator compounds may take the form of small organic molecules, antibodies (monoclonal or polyclonal and/or antigen (fish-associated sequence) binding fragments thereof) with affinity for any of the fish-associated sequences described herein (such antibodies are described above), proteins, peptides, carbohydrates, nucleic acids (RNA and/or DNA), aptamers.

One of skill in this field will appreciate that compounds which exhibit an ability to modulate (for example increase or decrease) aspects of the function, expression and/or activity of any of the fish-associated sequences of this invention may easily be prepared and tested. For example, a compound (a test agent) may be tested for an ability to modulate a fish-associated sequence of this invention by contacting the agent with an S. agalactiae strain expressing one or more of the fish-associated sequences of this invention and determining (perhaps after a period of incubation) any modulation of the level of expression, function and/or activity of the fish associated sequence.

Modulation of a level of expression, function and/or activity of a fish-associated sequence may be determined by comparison with the level of expression function and/or activity of the same or a corresponding fish-associated sequence(s) in a control system—for example an S. agalactiae strain which has not been contacted with the test agent. The detection of any difference in the expression, function and/or activity of one or more of the fish-associated sequences indicates that the test agent may be a compound which is capable of modulating the expression, function and/or activity of one or more of the fish-associated sequences.

Compounds which modulate the expression, function or activity of one or more of the fish-associated sequences (for example compounds which block or neutralize the function, expression or activity of a fish-associated sequence) may find application (as medicament) in the treatment or prevention of diseases, conditions or infections caused or contributed to by S. agalactiae in fish. Such compounds may also be useful in methods of treating or preventing diseases, conditions or infections caused or contributed to by S. agalactiae in fish, the methods comprising administering therapeutically effective amounts of the compounds described herein.

The invention further provides a method of raising an anti-Streptococcus agalactiae immune response in an animal, said method comprising the step of administering to an animal, an immunogenic amount of one or more Streptococcus antigen(s) or fragment(s) thereof, sufficient to induce an anti-Streptococcus agalactiae immune response.

The vaccines, vaccine/immunogenic compositions and antigens of this invention may find application in the treatment, prevention and/or control of S. agalactiae infections and/or associated diseases in fish hosts. The vaccine may be a polypeptide or polynucleotide vaccine—the polypeptides and/or polynucleotides providing, or encoding, one or more of the S. agalactiae fish-associated sequences/antigens described herein.

The vaccines, vaccine/immunogenic compositions and antigens of this invention may be used not only to raise immune responses in animals (in particular fish) but also in the treatment or prevention of diseases caused or contributed to by streptococcal species, including for example, S. agalactiae. The various therapeutic agents discussed herein (vaccines, immunogenic compositions, antigens and the like) may be used to treat or prevent diseases such as, for example, septicaemia and meningo-encephalitis as might occur in freshwater and saltwater fish species. Thus, the immunogenic compositions, vaccines and antigens of this invention have significant utility in any fish species susceptible or predisposed to a disease, condition or infection caused or contributed to by a streptococcal species or, more specifically, by S. agalactiae. For example, the vaccines, immunogenic compositions and antigens of this invention may be used to raise immune responses and/or prevent or treat diseases and/or infections (such as S. agalactiae-associated diseases, conditions or infections) in tilapia.

The compositions of this invention, including, for example the immunogenic and vaccine compositions, may be formulated for enteral (including oral), topical (including dermal and sublingual), parenteral (including subcutaneous, intradermal, intramuscular, intraperitoneal and intravenous), transdermal and/or mucosal administration. The compositions of this invention, including, for example the immunogenic and vaccine compositions, may be formulated for "immersion" or "bath" administration—specifically, the compounds may be added to water into which an animal (for example a fish) to be treated is placed. As the fish passes water through its body and over its gills, it is brought into contact with any compositions that have been added to the water.

DETAILED DESCRIPTION

The present invention will now be described in detail with reference to the following Figures which show:

FIG. 1: Kaplan-Meier curves comparing survival of tilapia following intraperitoneal injection of *Streptococcus agalactiae* strain STIR-CD-17 (sequence type (ST) 260) at doses corresponding to $10^2$, $10^5$ and $10^7$ cfu per fish. No mortality was observed for the negative control fish (sham dose). Curves are significantly different (Mantel-Cox log rank test, $P<0.05$).

Figure 2:
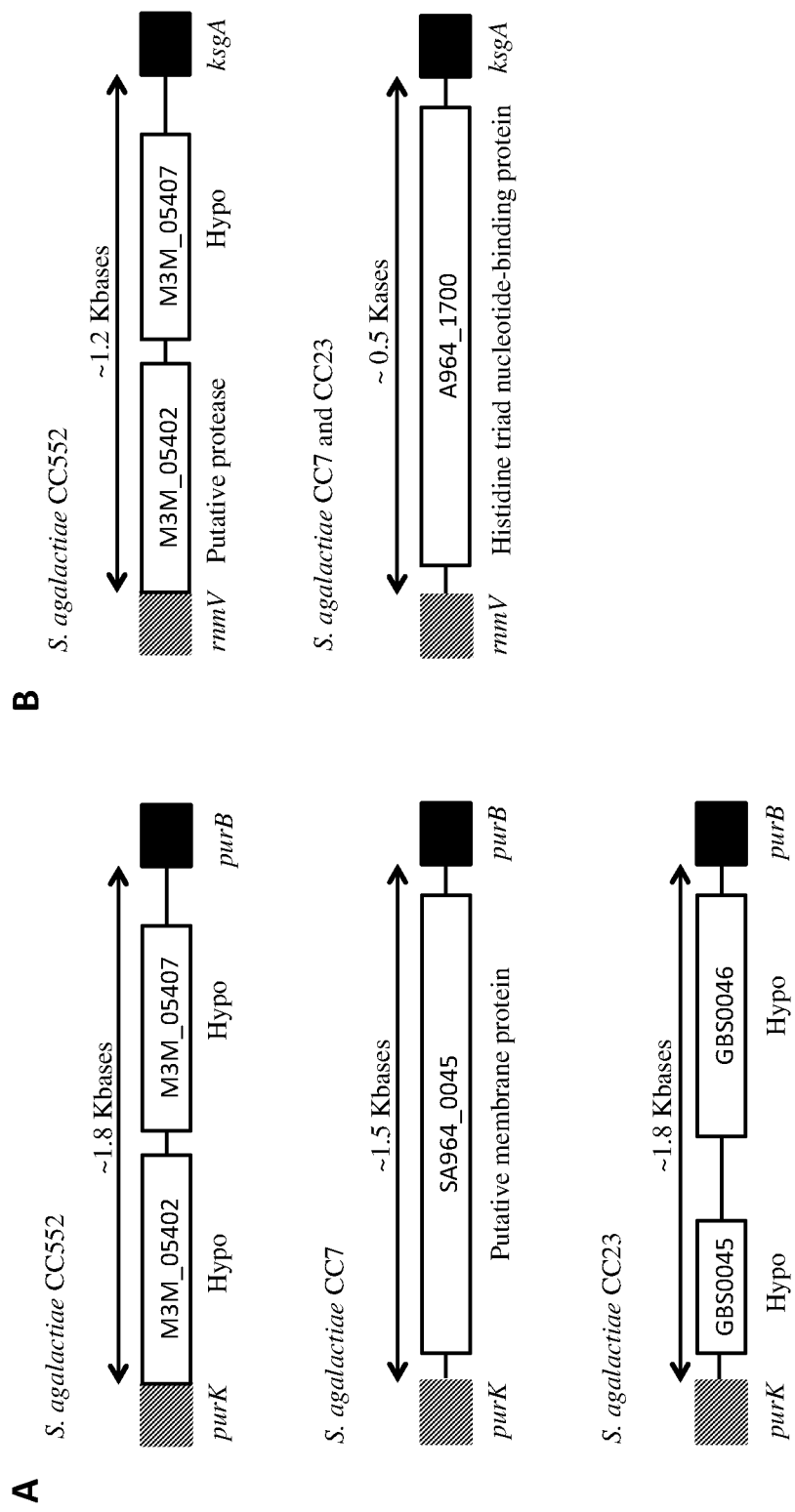

FIG. 2: Minimal mobile elements containing fish specific genes are clustered in Locus 1 (A), with clonal complex (CC) specific genomic content inserted between flanking genes purK and purB, and in Locus 8 (B), which shows lineage-specific content for CC552 but not for other CCs of *Streptococcus agalactiae*. In this analysis, CC552 includes isolates STIR-CD-17 and SA20-06; CC7 includes isolates GD201008-001, ZQ0910 and A909; and CC23 includes isolates NEM316, 515 and MRI Z1-201. Hypo=hypothetical protein.

Figure 3:
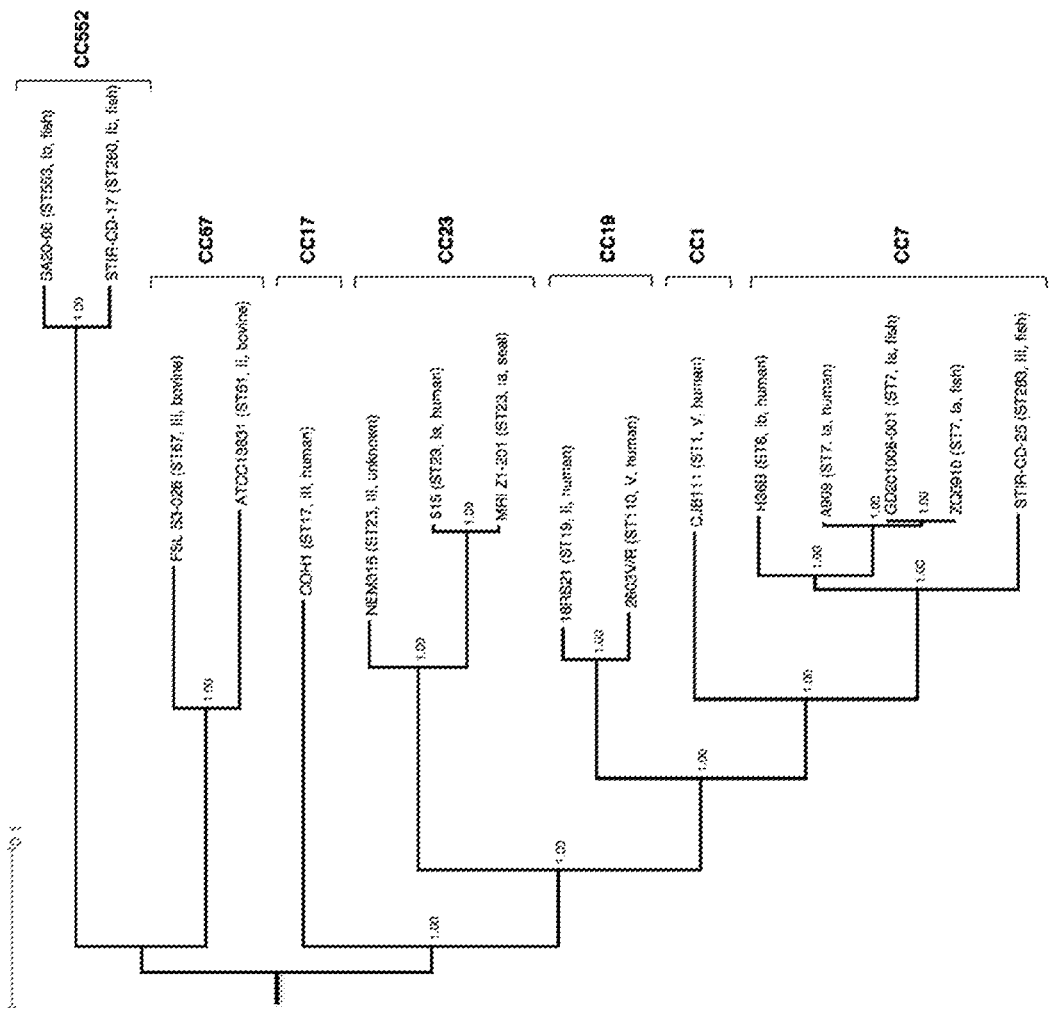

FIG. 3: Bayesian phylogenetic tree based on 22,484 concatenated SNPs from the core genome of 16 isolates of *Streptococcus agalactiae* showing sequence type (ST), serotype and host of origin (fish, seal, bovine, human or unknown origin). Clonal complex (CC) of isolates included in the analysis are also indicated, using nomenclature that predates the amalgamation of CC1, CC7, CC17 and CC19. Posterior probabilities are shown at each node and the scale bar represents the substitutions per site.

Figure 4:
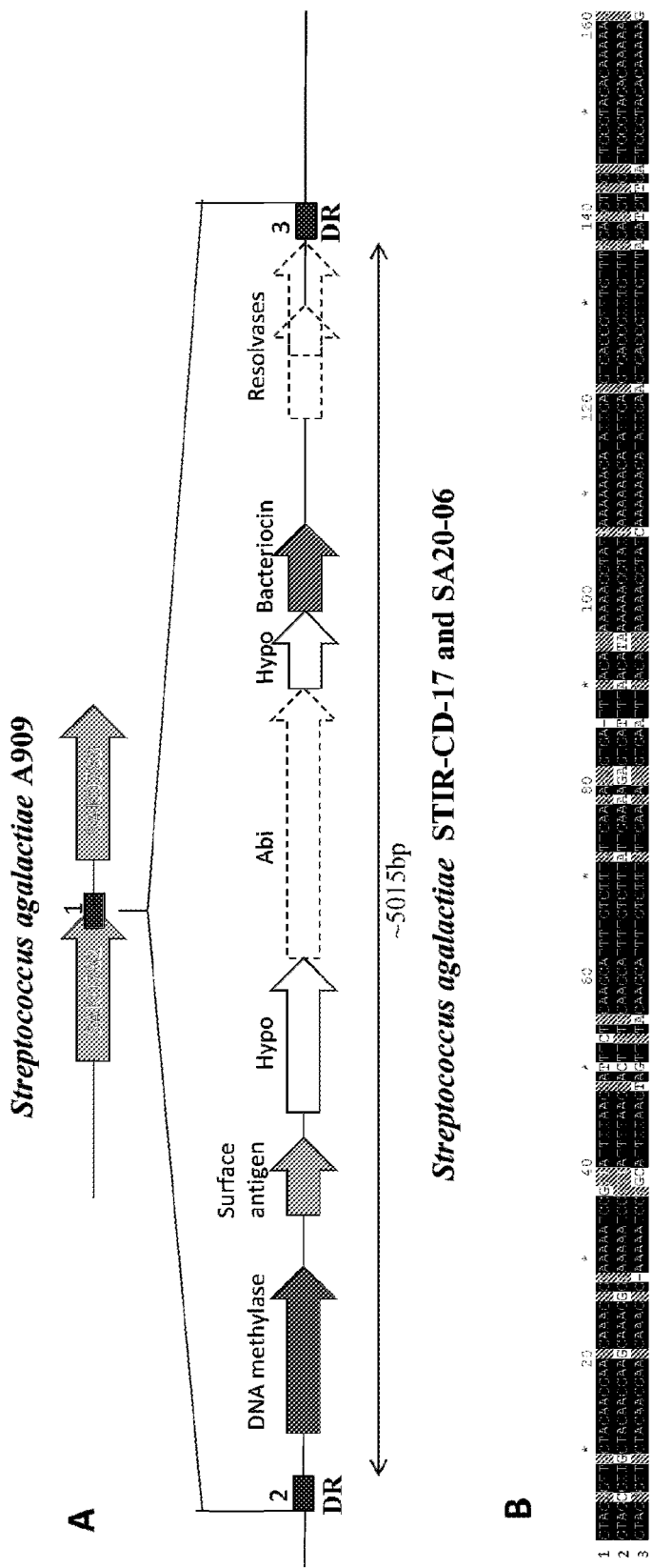

FIG. 4: (A) Genetic structure of locus 5, which carries 5 genes (full arrows), and 3 pseudogenes (dashed arrows). Locus 5 disrupts a conserved gene encoding a putative outer-membrane protein in *S. agalactiae* A909 (ST7). Direct repeats (DR) flank the extremities of locus 5 and a similar sequence is found in the corresponding integration position in *S. agalactiae* A909. (B) Alignment of the DR sequences as found in STIR-CD-17 (sequence 2 and 3) with the corresponding sequence as found in A909 (sequence 1). Black blocks indicate sequence identity and grey blocks indicate single nucleotide polymorphisms. Hypo, Hypothetical protein; Abi, abortive infection protein.

Figure 5:
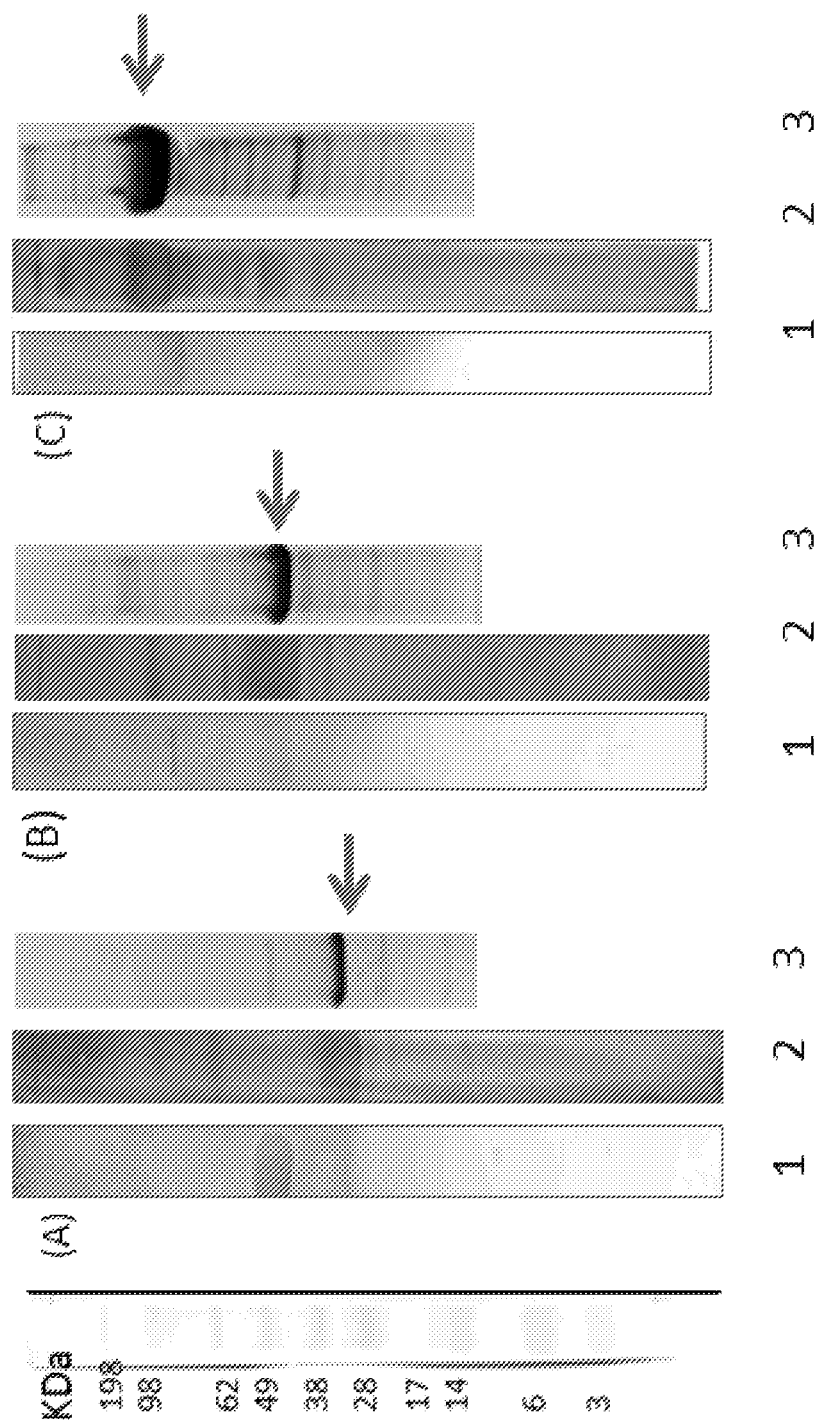

FIG. 5: Western blot of *Streptococcus agalactiae* recombinant proteins (SDS-PAGE 4-12% Bis-Tris polyacrylamide gel). (A) M3M-01212—rhamnulose-1-phosphate aldolase; (B) V193-02470—aldose epimerase; (C) M3M-01172—alpha-galactosidase. Lanes: (1) negative control fish serum (1/20; (2) immunised fish serum (1/20); (3) Coomassie blue stained gel. Band of interest is indicated with an arrow.

MATERIALS AND METHODS

Challenge Study
  *Streptococcus agalactiae* Strains.
  For the challenge study, isolates representing CC552 and ST23 were selected. CC552 was represented by isolate STIR-CD-17, which was isolated in 2008 during a clinical outbreak of streptococcosis affecting farmed tilapia (*Oreochromis* sp.) in Honduras. This isolate is non-haemolytic, belongs to ST260 and serotype Ib and it was negative by PCR for all surface protein genes and mobile genetic elements (MGE) that were evaluated as part of standardized 3-set genotyping (Delannoy et al. 2013). ST23 was represented by isolate MRI Z1-201, which was recovered by lung swab from a grey seal (*Halichoerus grypus*) found dead in 2003 in Scottish coastal waters. Post-mortem examination of the seal identified a systemic infectious process as the cause of death, but it was not clear whether this was caused by the *S. agalactiae* strain. MRI Z1-201 is beta-haemolytic, belongs to serotype Ia and contains genes encoding an alpha-like protein (alp1) and 3 insertion sequences (IS1381, ISSag1 and ISSag2) (Delannoy et al., 2013). This combination of ST, molecular serotype, surface protein-encoding genes and insertion sequences has been reported from poikilothermic animals, including being a cause of necrotizing fasciitis in crocodiles (*Crocodylus porosus*) (Bishop et al. 2007).

Fish.
  Nile tilapia (*Oreochromis niloticus*) were reared in the Tropical Aquarium at the Institute of Aquaculture (University of Stirling, UK) and maintained in a re-circulating water system in aquaria at 28±2° C. under constant aeration and filtration. The fish were fed twice daily with commercial pellets (Skretting, UK) and kept on a 12 h light/12 h dark cycle. Prior to bacterial challenge, three fish were sacrificed and sampled for bacterial recovery as described (Crumlish, Thanh, Koesling, Tung & Gravningen 2010); briefly, a sterile plastic bacteriological loop (Fisher Scientific, Loughborough, UK) was inserted into the kidney and used to inoculate a tryptone soya agar plate (TSA; Oxoid Ltd., Basingstoke, UK). Plates were incubated at 28° C. for 72 h and examined for the presence of bacterial colonies. Absence of microbial colonisation was confirmed, and clinically healthy animals originating from the same groups and weighing 40±5 g were transferred to the Aquatic Research Challenge Facility (Institute of Aquaculture, University of Stirling, UK) for subsequent use in passage and challenge studies. All animal experiments were conducted at the Institute of Aquaculture in accordance with the Animals (Scientific Procedures) Act 1986.

Passage and Challenge.
  Fish were lightly anaesthetized by immersion in a benzocaine bath (Sigma-Aldrich, Irvine, UK). For intraperitoneal (i.p.) challenge, a 0.1 mL inoculum was administered via a needle, mounted on a 1 mL syringe, inserted cephalad into the midline of the abdomen just posterior to the pectoral fins. Fish were fasted for 24 h prior to injection and for 12 h following injection, at which time daily feeding was resumed. Fish from different experimental groups (10 animals per group), as defined by strain, dose and follow-up period, were kept in separate 10 L aquaria with separate flow-through water systems, a temperature of 28±2° C. and a 12 h light/12 h dark cycle. Fish were monitored at least 3 times daily for signs of disease and death. All moribund and dead fish were removed, and moribund fish were euthanized with an overdose of benzocaine.

Prior to the challenge experiment, ST260 and ST23 were passaged through fish to enhance their virulence post-storage (Eldar, Bejerano, Livoff, Horovitcz & Bercovier 1995). For each strain, a single colony from a pure culture was used to inoculate 4 mL of tryptone soya broth (TSB; Oxoid Ltd.) and cultures were incubated aerobically for 8 h (ST23, fast growing) or 24 h (ST260, slow growing) at 28° C. with gentle shaking (140 rpm). These cultures were then used to seed 36 mL aliquots of TSB, and cultures were incubated for 16 h at 28° C. and 140 rpm. Cultures were then centrifuged at 3,293 rcf for 15 min and the supernatants were discarded. Centrifugation was repeated several times for ST260 because it produced a fragile cell pellet. Cell pellets were resuspended in sterile 0.85% saline and the $OD_{600\,nm}$ was adjusted to 1, corresponding to approximately $10^9$ viable colony forming units (cfu) per mL for ST260 and $10^8$ viable cfu per mL for ST23, as determined by plating serial ten-fold dilutions according to the method of Miles, Misra & Irwin (1938). Inocula containing a high concentration of bacteria (approximately $10^7$ cfu per fish) were injected into a single fish. For ST260, this procedure was only performed on a single occasion, because the fish died as a direct consequence of infection within 3 days post-inoculation (p.i.). Fish challenged with ST23 were euthanized at 3 days p.i., *S. agalactiae* was cultured from the brain and kidney and the procedure was repeated twice, whereby isolates from the sacrificed fish were used to prepare the inoculum for the next passage. One colony isolated from the brain after the 1$^{st}$ passage (ST260) or the 3$^{rd}$ passage (ST23) was sub-cultured onto 5% (v/v) sheep blood agar plates (SBA; E&O Laboratories, Bonnybridge, UK) and used for challenge experiments.

Based on results from the pre-experimental passages, challenge with ST260 was conducted at three doses ($10^2$, $10^5$ and $10^7$ cfu per mL; 3 groups of 10 animals each) whereas challenge with ST23 was only conducted at the highest dose ($10^7$ cfu per mL; 2 groups of 10 animals each). A sixth group (10 animals) was mock-challenged with 0.85% sterile saline. The maximum follow-up period was 16 days. For fish challenged with ST260, moribund individuals were euthanized as well as the fish remaining at day 16 p.i. For fish challenged with ST23, one group was euthanized at day 7 p.i. while the second group and the negative control group were euthanized at day 16 p.i. Euthanized fish were aseptically sampled for bacterial recovery from the kidney (Crumlish et al. 2010). Kaplan-Meier curves were used to compare survival rates of tilapia challenged with different doses of ST260 and significance of differences was determined using a log rank test (Graph Pad Software version 5, San Diego, Calif., USA).

Genome Comparison
  Genomic DNA Preparation.
  The ST260 isolate, STIR-CD-17, was streaked onto SBA and grown aerobically at 28° C. for 72 h to assess purity and absence of haemolysis. A single colony was used to inoculate 5 mL of Brain Heart Infusion broth (BHI; Oxoid Ltd.). After overnight static incubation at 28° C. in an aerobic environment, genomic DNA was extracted from cells harvested from 1 mL of culture using an Epicentre MasterPure Gram-positive DNA purification kit (Epicentre, Madison, Wis., USA), with slight modifications; briefly, the bacterial culture was repeatedly centrifuged (due to loose pellet), supernatant was removed and cells were re-suspended in 150 µL of TE Buffer (10 mM Tris-HCl (pH 7.5), 1 mM EDTA), 6 µL of mutanolysin (5 U per µL; Sigma-Aldrich, Irvine, UK) and 1 µL of ready-to-use lysozyme (as provided by the kit manufacturer), and incubated at 37° C. for 1 h. The remainder of the protocol was performed according to manufacturer's instructions, except for the extension of the Proteinase K/Gram-Positive Lysis Solution incubation time (30 min instead of 15 min) and the RNase incubation time (1 h instead of 30 min). DNA concentration was quantified using a NanoDrop 1000 (Thermo Scientific, Loughborough, UK) and genomic DNA (0.5 µg) was visualized over UV light to assess absence of shearing following electrophoresis through a Gel Red (Cambridge Bioscience, Cambridge, UK)—containing 0.8% (w/v) agarose gel (at 100 V cm$^{-1}$ for 1 h).

Genome Sequencing, Assembly and Annotation. Genome sequencing and de novo assembly of reads was performed at the GenePool sequencing core facility (University of Edinburgh, UK) using an Illumina Solexa Genome Analyzer and VELVET 0.6. Of 208 contiguous sequences (contigs), 96 were more than 200 nucleotides long and were annotated using the Prokaryotic Genomes Automatic Annotation Pipeline (PGAAP) of the National Centre for Biotechnology Information (NCBI). The draft genome sequence of *S. agalactiae* STIR-CD-17 has been deposited in GenBank under accession number ALXB00000000 (Delannoy, Zadoks, Lainson, Ferguson, Crumlish, Turnbull & Fontaine 2012). Functional categories of proteins were identified by PGAAP based on the analysis of Clusters of Orthologous Genes (COGs) using the COGnitor program (Tatusov, Fedorova, Jackson, Jacobs, Kiryutin, Koonin, Krylov, Mazumder, Mekhedov, Nikolskaya, Rao, Smirnov, Sverdlov, Vasudevan, Wolf, Yin & Natale 2003). When a functional category could not be identified using COG analysis, nucleotide sequences were screened for conserved Pfam domains (http://pfam.sanger.ac.uk/search) to determine the putative function of hypothetical proteins. Finally, in silico prediction of subcellular localization of proteins encoded by the genome was performed using the PSORTb program version 3.0.2 (Yu, Wagner, Laird, Melli, Rey, Lo, Dao, Sahinalp, Ester & Foster 2010), using the module for Gram-positive bacteria. Prediction categories included cytoplasmic, cytoplasmic membrane, cell wall, extracellular and unknown localization.

Comparative Genomic Analysis.

For comparative analysis, representative *S. agalactiae* genomes were selected, including those from subpopulations found in fish and humans (CC7), in terrestrial and aquatic mammals but not in fish (CC23), in humans only (CC17), in cattle only (CC67), and in humans and cattle (CC1, CC19) (Delannoy et al. 2013; Zadoks et al. 2011).

Genomes were compared by means of reciprocal BLAST comparison of the translated products of predicted open reading frames (ORF) of STIR-CD-17 against each of 10 reference genomes (Table 2). The BLASTP score was used to express the level of homology and to identify reciprocal best hits. Predicted protein sequences from STIR-CD-17 that did not find a reciprocal best hit with a BLAST score >80 in any of the other genomes were identified, and their corresponding genes were considered putatively fish-specific. Predicted protein sequences from STIR-CD-17 with a reciprocal best hit and BLAST score >80 in genomes belonging to CC7 only were also identified, and their corresponding genes were considered putatively fish-associated because isolates belonging to CC7 occur in fish as well as in people. Subsequently, amino acid sequences encoded by the predicted putatively fish-specific or fish-associated genes were searched against the NCBI protein database (http://www.ncbi.n-lm.nih.gov/BLAST; last accessed 13 Jan. 2013) to determine whether homologues existed beyond the 10 selected *S. agalactiae* genomes. Homology between predicted proteins was analysed whilst correcting for query length using normalised BLAST score ratio (BSR) analysis (Rasko, Myers & Ravel 2005). For each protein, the BLASTP bit-score for the alignment against itself (REF_SCORE) and for the most similar proteins within the database (QUE_SCORE) was obtained and normalized by dividing the QUE_SCORE by the REF_SCORE. Amino acid sequences with a normalized bit-score ≥0.8 were considered homologous. Normalized bit-scores <0.8 were taken as an indication of divergence (0.4<BSR<0.8) or uniqueness (BSR≤0.4) (Rasko et al. 2005). Finally, to overcome potential annotation discrepancies, selected genomes were compared pairwise using the Artemis Comparison Tool (ACT; Carver, Berriman, Tivey, Patel, Bohme, Barrell, Parkhill & Rajandream 2008) and the DOUBLE ACT v2 web interface (http://www.hpa-bioinfotools.org.uk/pise/double_act.html) with BLASTN and default settings. The ACT comparison also provided insight into the genetic organisation and conservation of sequences flanking regions of interest.

Finally, the genome of STIR-CD-17 (ST260) was compared with the unannotated genome of MRI Z1-201 (ST23; NCBI accession number ANQL00000000). Both genomes were analysed by BLAST search and ACT comparisons for the presence of known *S. agalactiae* virulence genes, including adhesins, invasins and evasins (Table 3). Pairwise ACT comparisons between STIR-CD-17 and MRI Z1-201 were also performed to evaluate presence of the putatively fish-specific genes and fish-associated genes within MRI Z1-201 and results were confirmed by PCR (discussed below). Lastly, the relatedness between the challenge study isolates and other fish-derived *S. agalactiae* isolates was explored based on the phylogeny of their core genome. In addition to the challenge study isolates and the annotated genomes listed in Table 2, this analysis included genomes of the fish-derived isolates SA20-06 (ST553; Pereira, Rodrigues, Hassan, Aburjaile, Soares, Ramos, Carneiro, Guimarães, Silva, Diniz, Barbosa, Gomes de Sã, Ali, Bakhtiar, Dorella, Zerlotini, Araújo, Leite, Oliveira, Miyoshi, Silva, Azevedo & Figueiredo 2013), ZQ0910 (ST7; Wang, Jian, Lu, Cai, Huang, Tang & Wu 2012), GD201008-001 (ST7; Liu, Zhang & Lu 2012) and STIR-CD-25 (ST283; NCBI accession number ANEK01000001; Delannoy et al. 2013). The Panseq v.2.0. Web server (Laing, Buchanan, Taboada, Zhang, Kropinski, Villegas, Thomas & Gannon 2010) was used for automated extraction, concatenation and alignment of nucleotide sequences from the core genome, using default settings except that the core genome threshold was set to 16 so that any region not found in all 16 genomes was removed. The resulting nexus file consisting of 22,484 concatenated single-nucleotide polymorphisms (SNPs) from the core genome was used for phylogenetic analysis and model optimisation in TOPALi v2.5 (Milne, Wright, Rowe, Marshall, Husmeier & McGuire 2004). The selected model (Symmetrical Model [SYM]) was used to estimate a Bayesian phylogenetic tree in MrBayes (Ronquist & Huelsenbeck 2003) launched from TOPALi. The MrBayes settings were 2 runs of 625,000 generations and a burn-in period of 125,000 generations, with trees sampled every 10 generations. The consensus tree was imported into DENDROSCOPE v3.2.1 (Huson, Richter, Rausch, Dezulian, Franz & Rupp 2007) for visualization and editing.

Population Screening

Isolate Collection.

To complement the in silico identification of putatively fish-specific or fish-associated genes, which was largely based on comparison with S. agalactiae of human origin, the presence of genes of interest was assessed among a panel of unsequenced S. agalactiae isolates from fish, aquatic mammals and cattle. Fish and sea mammal isolates used have previously been described in detail (Delannoy et al. 2013). Briefly, fish isolates originated from an outbreak of streptococcosis in wild mullet (Liza klunzinger) in Kuwait (1 outbreak, 5 isolates), from outbreaks of streptococcosis in farmed tilapia (Oreochromis spp.) from Colombia (1 outbreak, 1 isolate), Costa Rica (1 outbreak, 4 isolates), Honduras (1 outbreak, 3 isolates), Vietnam (1 isolate), Thailand (7 isolates from 7 unrelated outbreaks) and Belgium (1 isolate) and from 3 fish (rosy barb, golden ram, and unidentified species) from unrelated aquaria in Australia. Thus, 16 epidemiologically unrelated events were represented. The sequenced strain, STIR-CD-17, originated from the outbreak in Honduras. Sea mammal isolates originated from a bottlenose dolphin (Tursiops truncatus) and 5 grey seals (Halichoerus grypus) that had stranded in the UK in unrelated incidents. Bovine isolates were obtained from aseptically collected quarter milk samples from 6 farms in Denmark and, based on pulsed-field gel electrophoresis and multi-locus sequence typing (unpublished data), represented 19 macro-restriction profiles and 6 STs from 3 CCs (CC1, 19 and 23).

PCR Screening.

Final volumes of 250 µL of bacterial lysates were prepared by digestion with lysozyme and proteinase K (Delannoy et al. 2013). Species identity of all isolates was confirmed using primers that target a species-specific fragment of the 16S-23S intergenic spacer region (Delannoy et al. 2013). Intragenic primers were designed from the genome of STIR-CD-17 to allow amplification of 2 putatively fish-specific genes and 3 fish-associated genes using the Primer Select module in Lasergene (DNASTAR Inc., Madison, Wis., USA) (Table 4). PCR reactions for species confirmation and detection of putatively fish-specific and fish-associated genes were performed in 25 µL volumes containing 12.5 µL of GoTaq Green Master Mix (Promega, Madison, Wis., USA), 0.25 µM of each primer and 2 µL of DNA template. Thermal cycling consisted of a denaturation step at 94° C. for 5 min followed by 35 cycles of 94° C. for 1 min, target-specific annealing temperature for 45 s, and 72° C. for 30 s with a final step at 72° C. for 7 min. Annealing temperatures were based on the melting temperatures of the respective primer sets, as provided by the manufacturer (Eurofins MWG Operon, Munich, Germany). The PCR products for all reactions were visualized over UV light following electrophoresis through 1.5% (w/v) agarose gels containing Gel Red. Strain STIR-CD-17, from which the genome and primer sequences were derived, was included in each assay as positive control and a water blank was included as negative control.

Results

Challenge Study

Fish challenged with ST260 showed dose-dependent mortality (FIG. 1). Most deaths occurred between days 1 and 7 p.i., and at termination of the experiment only 1 fish remained alive. Fish that died within 48 hr p.i. did not show any clinical signs of disease prior to death. The first clinical signs appeared 2 to 5 days p.i. depending on the dose administered, and consisted of lethargy and anorexia which were always followed by signs of ataxia 24 to 48 h prior to death. Most fish remaining alive after day 7 (only fish from the groups receiving $10^2$ and $10^6$ cfu per fish) exhibited uni- or bilateral exophthalmia together with corneal opacity and peri-ocular haemorrhage. Occasionally, fish exhibited abdominal extension due to accumulation of ascitic fluid ranging from translucent to purulent. Streptococcus agalactiae was recovered from the kidneys of all tested tilapia (n=10).

Among fish challenged with ST23, no mortality or clinical signs were observed after 7 days p.i. One group of 10 fish was sacrificed and bacteria were recovered from the kidneys of 3 of these fish, demonstrating infection in the absence of clinical disease. After day 7, there was one dead fish but death was attributed to fighting and cannibalism. Sampling for bacterial recovery was not possible for this fish due to absence of its carcass. The second group of 10 fish was euthanized at the end of the experiment (16 days p.i.). No bacteria were recovered from the kidneys of this group. No morbidity or mortality was recorded in mock-challenged control fish nor were any bacteria recovered from these fish.

Genome Comparison

The draft genome of STIR-CD-17 contained 1,805,303 nucleotides, 21 rRNA genes and 80 tRNA genes. The average G+C content was 35%. In addition, 102 pseudogenes were identified which contained multiple stop codons due to frameshift and nonsense mutations.

Several putatively fish-specific genes and fish-associated genes were identified (Table 1). Genes were considered to be putatively fish-specific if they were identified only in the genome of ST260 during whole genome comparison and only in isolates from CC552 in subsequent BSR analysis, which included additional sequence information from NCBI. Genes were considered to be fish-associated if they were only identified in the genome of ST260 and ST6 or ST7 (both CC7) during whole genome comparison and only in isolates from CC552 or CC7 in subsequent BSR analysis but not in members of other CCs. Putatively fish-specific and fish-associated genes were distributed over 8 small clusters or loci, which are discussed in the following sections. The largest locus, locus 3, was considered fish-associated whereas the remaining 7 loci were fish-specific. Locus 4 included a few genes that were shared with other strains of S. agalactiae, implying that some elements of this locus were not fish-specific; however, rather than being split into multiple fish-specific and non-specific elements, this locus will be described as if it were fish-associated. The first and last loci, namely locus 1 and locus 8, were located between sets of genes considered well-conserved across S. agalactiae genomes. Locus 1 contained two fish-specific ORF, the translated products of which were predicted to be localised within the cytoplasm (due to the absence of any secretion-associated motifs), but did not contain any known domain from which a putative function could be derived. The 2 ORF were located between genes (purK and purB encoding an ATPase subunit and an adenylosuccinate lyase, respectively) that are well-conserved across S. agalactiae genomes, including those from fish. ACT comparison of genomes from different CCs showed that the region delimited by purK and purB is occupied by distinct genes in different lineages, whereas the region is identical between isolates that belong to the same CC. For example, the same hypothetical proteins were found in the genome of 2 piscine isolates belonging to CC552 (STIR-CD-17 and SA20-06), whereas a putative membrane protein was shared by CC7 strains of human and piscine origin (A909 and GD201008-001 and ZQ0910) (FIG. 2A). Locus 8 also contained 2 fish-specific ORF, the first of which was predicted to encode a putative cytoplasmic protein containing a conserved domain of unknown function (PF08002). The translated product of the second ORF was identified as a DJ-1/Pfp1 family protein (COG0693/PF01965), which includes proteins with intracellular protease function or transcriptional regulators (Halio, Blumentals, Short, Merrill & Kelly 1996; Ohnishi, Yamazaki, Kato, Tomono & Horinouchi 2005). As in locus 1, the ORF were inserted between 2 well-conserved genes, in this case ksgA (encoding a 16S ribosomal RNA methyltransferase KsgA/Dim1 family protein) and rnmV (encoding a primase-like protein). Locus 8 showed less diversity than locus 1, whereby the observed sequence in isolates from CC552 was conserved and distinct from the sequence in isolates from other CCs, but isolates from CC7 and CC23 contained homologous regions between ksgA and mmV (FIG. 2B).

Locus 2, 3 and 4 were all found close to each other, with locus 3 located approximately 1.7 kb downstream of locus 2, and locus 4 approximately 5.1 kb downstream of locus 3. Locus 2 was located within putative pathogenicity island (PAI) IV from human *S. agalactiae* (Glaser, Rusniok, Buchrieser, Chevalier, Frangeul, Msadek, Zouine, Couve, Lalioui, Poyart, Trieu-Cuot & Kunst 2002; Herbert, Beveridge, McCormick, Aten, Jones, Snyder & Saunders 2005), and contained a single ORF, the translated product of which was predicted to encode a cytoplasmic protein of unknown function. This ORF was only found within the genomes of CC552 isolates. Based on ACT comparison, this fish-specific gene occupied the region that contains the virulence genes rib or bca in genomes of human *S. agalactiae*, genes that are absent from CC552 isolates (Delannoy et al. 2013; this study). Locus 3 was located just external to PAI IV (inserted between gbs0486 and gbs0487 in NEM316, PAI IV being delimited by gbs0458-0486; Glaser et al. 2002; Herbert et al. 2005) and comprised 18 ORF. The translated products shared homology with proteins found in all *S. agalactiae* from fish, i.e. isolates belonging to CC552 and CC7, and in human isolates belonging to CC7, but not with human isolates from other CCs. This locus therefore comprises genes designated as fish-associated in *S. agalactiae*, even though homologues of some genes were found in other streptococcal species (Table 1). With the exception of 1 ORF encoding a putative transcriptional regulator, the ORF in locus 3 encoded products predicted to be involved in carbohydrate transport and metabolism, including those involved in the transport and degradation of galactose (GalK, GalE, GalM) and the hydrolysis of galactose-containing oligosaccharides (GalA). Concerning locus 4, its composition and organisation was found to correspond to a CRISPR-cas module (clustered regularly interspaced short palindromic repeats-CRISPR associated proteins) with sequence identity to subtype IC (Makarova, Haft, Barrangou, Brouns, Charpentier, Horvath, Moineau, Mojica, Wolf & Yakunin 2011). Three ORF from this locus were found in *S. agalactiae* from CC552 only. Frame-shifts within 2 of the ORF in this locus resulted in the early termination of the coding sequences, meaning the resulting pseudogenes are unlikely be functional. Some components of the locus are also found in human or bovine strains of *S. agalactiae* belonging to ST17, ST23 and ST67, whilst other homologues of some elements are found in other streptococcal species such as *S. mutans, S. canis* and *S. dysgalactiae* subsp. *equisimilis* (Table 1).

Locus 5 and 6 were identified within PAI VI (Glaser et al. 2002; Herbert et al. 2005). Locus 5 was flanked by 159 bp direct repeats and integrated at the position of a similar 159 bp sequence into a conserved gene encoding a putative outer membrane protein in human *S. agalactiae* strains. Locus 5 was fish-specific and contained 5 ORF and 4 probable pseudogenes (FIG. 4). The translated product of the first ORF, although of unknown function, contained a conserved DNA methylase domain (PF00145). The second ORF encoded a putative surface-anchored protein containing a CHAP domain (pfam05257). The following 2 ORFs encoded hypothetical proteins only found in isolates from CC552, while the final ORF encoded a putative bacteriocin. The pseudogenes encoded a putative phage abortive infection protein, AbiGII and two resolvases; however, frameshift mutations in each resulted in premature termination of the coding sequence. Comparison of these 4 pseudogenes with the equivalent region in the SA20-06 genome revealed identical frame-shifts in each coding sequence. Locus 6 was located approximately 4.3 kb downstream from locus 5. Locus 6 was unique to STIR-CD-17, containing 5 ORF, 3 encoding hypothetical proteins with no domains of known function, 1 encoding a putative serine hydroxymethyltransferase (SHMT) and 1 encoding a putative integrase. The locus was integrated into and disrupted a gene with hypothetical function that is conserved among other strains of *S. agalactiae*.

Locus 7 was composed of 8 ORF, of which 3 were unique to STIR-CD-17 and 5 where shared with SA20-06 (CC552), making the latter fish-specific by our terminology. The 3 unique ORF encoded a putative permease, a putative beta-hydroxyl dehydratase involved in fatty acid biosynthesis (M3M_04280; PF07977) and a hypothetical protein. The translated products of the ORF that were shared within CC552 included two putative transcriptional regulators, two hypothetical proteins and a putative integrase, suggesting that these ORF form part of a MGE. Indeed, Locus 7 was inserted into a 6-phospho-beta-glucosidase-encoding gene, found intact in other *S. agalactiae* such as A909 (ST7).

Comparison of Challenge Strains

Numerous genes that are recognised as encoding virulence determinants in human *S. agalactiae* were present in the ST23 strain but not in the ST260 strain used for the challenge experiments (Table 3), including genes encoding adhesins (fbsA and lmb) and an immune evasin (scpB). Other genes were conserved in both strains, including those encoding putative adhesins (fbsA, pavA, srrl, and bibA), invasins (cfb and hylB) and immune evasins (cps and neu operon, ponA, and sodA). The allelic variants of bibA differed between ST260 (gbs2018-6) and ST23 (gbs2018-1; Brochet, Couve, Zouine, Vallaeys, Rusniok, Lamy, Buchrieser, Trieu-Cuot, Kunst, Poyart & Glaser 2006), as did pilus-encoding genes (PI2b in ST260 and PI-2a in ST23). In ST260, the backbone protein of PI2b was truncated, and a sortase appeared as a pseudogene due to the introduction of stop codons. Unlike ST23, ST260 was found to have an incomplete cyl operon, where only cylA and incomplete cylE and cylB were present. Based on ACT analysis, the non-virulent ST23 isolate did not contain fish-specific or fish-associated genes that were identified through comparison of annotated genes.

Phylogenetic analysis of the core genome showed that CC552 is distantly related to ST23, CC7 and other strains found in cattle and humans (FIG. 3). Within ST23, challenge strain MRI Z1-201 was genetically highly similar to human reference strain 515. Both strains belong to serotype Ia and were genetically divergent from NEM316, which belongs to ST23 and serotype III; in fact, the genetic distance between the serotype Ia and III isolates within ST23 was larger than the distance between distinct members of other clonal complexes, e.g. ST260 and ST553 in CC552, ST19 and ST110 in CC19, and ST6, ST7 and ST283 in CC7.

Population Screening

In silico analysis of genomic data from a limited number of S. agalactiae strains allowed the identification of putatively fish-specific and fish-associated genes. To determine whether the findings at genome level were representative of gene distribution at population level, a collection of isolates was screened by PCR for presence of the fish-specific genes M3M_04280 (locus 7) and M3M_01062 (locus 4) and the fish-associated genes M3M_01167, M3M_01172 and M3M_01182 (locus 3). The distribution of those targets across host species based on in silico analysis and PCR screening is shown in Table 5. Five profiles of gene presence/absence were identified, ranging from lack of detection of any of the 5 target genes (Profile 1) to detection of the full complement of target genes (Profile 5). Profile 1 was the most common, and was associated with isolates from multiple homeothermic species (humans, cattle and seals), multiple CCs (CC1, CC17, CC19, CC23 and CC67) and multiple continents. Profile 5 was associated exclusively with ST260, with all representatives of this ST having originated from disease outbreaks in farmed tilapia in South America. ST261, which can also be considered a member of CC552 (Delannoy et al., 2013), lacked the M3M_01062 amplicon, whilst testing positive for the remaining targets. This profile, Profile 4, was not uniquely associated with ST261 but was shared with ST7 isolates from a natural outbreak of disease in mullet in Kuwait. Other ST7 isolates from fish and from humans were positive for 3 or 4 target genes, resulting in 2 additional profiles (Profiles 2 and 3). Profile 2 was associated with human and piscine isolates from Thailand, China and the USA. Profile 3 was identified in piscine isolates from 2 continents (Asia and South America) and 2 CCs (CC7, including ST283, and CC552). There was a strong correlation between PCR profile, host species and ST, with two notable exceptions: one bovine isolate of ST1 was PCR-positive for the 3 fish-associated genes, and one dolphin isolate of ST399 was PCR-positive for the 3 fish-associated genes as well as one of the two putatively fish-specific genes.

Western Blots (FIG. 5)

The blots show that fish immunized with S. agalactiae proteins (M3M-01212 (-rhamnulose-1-phosphate aldolase), V193-02470 (aldose epimerase) and M3M-01172 alpha-galactosidase) raise an immune response against the immunogen. The same immune response was not seen in the control, non-immunised, fish. It should be noted that the multiple 'other' bands in each lane derive from the fact that the recombinant proteins were not 100% purified, and so the fish were also effectively "immunized" with other (unrelated) material from the expression host.

DISCUSSION

Despite the wide range of S. agalactiae STs and CCs associated with carriage and disease in humans, the only CCs to be associated with disease in fish are members of CC7 and CC552. Even ST23, which has a host range including humans, cattle, dogs, aquatic mammals (seals) and poikilotherms (crocodiles) (Bishop et al. 2007; Brochet, Couve, Zouine, Vallaeys, Rusniok, Lamy, Buchrieser, Trieu-Cuot, Kunst, Poyart & Glaser 2006; Delannoy et al. 2013, Sorensen, Poulsen, Ghezzo, Margarit & Kilian 2010), has not been identified in fish. Within ST23, two subpopulations are recognized, one predominantly associated with humans and belonging to serotype Ia and the other predominantly associated with cattle and belonging to serotype III (Sørensen et al 2010). Phylogenetic analysis of the core genome shows that the two subpopulations are genetically distinct, despite sharing ST23 (FIG. 3). Neither ST23 serotype Ia (this study) nor ST23 serotype III (Mian et al. 2009) cause disease in tilapia after intraperitoneal challenge. We demonstrated the presence of our ST23 strain in the brain and kidney of tilapia at 3 to 7 days post-challenge, but the infection remained asymptomatic and was cleared by day 16 p.i. Numerous genes recognised as encoding virulence determinants in human S. agalactiae are present in the genome of ST23 but not ST260 (Table 3), including genes encoding adhesins (fbsA, lmb) and an immune evasin (scpB). Absence of scpB has also been reported for bovine-associated S. agalactiae (Sorensen et al. 2010). Other genes were found to be only partially present or altered in STIR-CD-17, such as the genes from the Cyl operon and genes encoding the pilus 2b, explaining the non-haemolytic phenotype and suggesting the absence of pilus on the surface of STIR-CD-17.

The combination of challenge experiments and genomic analysis presented above shows that numerous known virulence genes do not contribute to disease in fish, implying that other virulence factors may play a role. Whilst previous authors have already observed that members of CC552 have a smaller genome than strains that affect other host species (approximately 1.8 Mb compared to 2.0 to 2.4 Mb for human and bovine derived S. agalactiae; Liu et al. 2013; Rosinski-Chupin et al. 2013), few efforts have been made to identify genome content that may explain virulence in fish. Using whole genome comparison, ACT analysis and BLAST score ratios we identified putatively fish-specific or fish-associated gene content. Fish-specific and fish-associated genes tended to be clustered in regions that carried signatures of MGEs, as previously described for bovine S. agalactiae (Richards et al. 2011). Supplementing the in silico analysis with PCR-based detection of 5 selected targets in a collection of field isolates from fish, sea mammals and cattle confirmed the exclusive or predominant association of these genes with CCs that are found in fish. All targets were detected in more than one ST, more than one host species and more than one country, but, with one exception, not in isolates from seals or cattle, nor in isolates belonging to CCs other than CC7 and CC552. One bovine isolate did not match the generic pattern whereby it belonged to CC1 and contained 3 genes that were clustered in locus 3. The fact that associations between genes and host species are rarely absolute has been demonstrated before in comparative analysis of human and bovine S. agalactiae populations (Richards et al. 2011). Based on the definition of CC sensu stricto (Feil, Li, Aanensen, Hanage & Spratt 2004), former CC1, CC7, CC17 and CC19 are currently all members of a single CC. To facilitate comparison with literature predating the amalgamation of those CCs, we have adhered to the old nomenclature and clusters. Based on analysis of the core phylogeny, ST283 was grouped under CC7 for the sake of the current discussion (FIG. 3).

Several fish-associated loci were flanked by conserved regions that can act as substrates for homologous recombination between strains, allowing for formation of minimal mobile elements (MMEs; Saunders & Snyder, 2002). For example, Locus 1 was located in the region between purK and purB (FIG. 2A). This region is a well-recognized MME containing variable inserts within the genome sequence of several pathogenic streptococci, including *Streptococcus pneumoniae* and *Streptococcus pyogenes* (Herbert et al., 2005). Locus 8 also fulfilled the criteria for an MME (FIG. 2B). In most *S. agalactiae* genomes of human isolates, this region is occupied by a histidine triad nucleotide-binding protein, which is replaced in *S. agalactiae* of CC552 by a hypothetical protein and DJ-1/Pfp family protein. This family includes proteins with intracellular protease function or transcriptional regulators (Halio et al., 1996; Ohnishi et al., 2005), but its role in fish-associated *S. agalactiae* is unknown. Locus 5 was not flanked by conserved regions but by direct repeats of 159 bp (Figure S1). The corresponding region for this locus is occupied by the same single 159 bp sequence in other *S. agalactiae* strains, suggesting that in STIR-CD-17 it may have been a MGE that lost its mobility through inactivation of resolvases, which were present as pseudogenes within the locus.

Presence of other MGEs was associated with putative integrases, e.g. for Locus 7 and 6. Locus 7 contained genes encoding products involved in fatty acid biosynthesis (PF07977) and a major facilitator family transporter (PF07690); the latter protein was predicted to be localised in the cytoplasmic membrane where it could contribute to transport of small solutes in response to chemiosmotic ion gradients (Pao, Paulsen & Saier 1998). Locus 6, which was found only in the genome of STIR-CD-17, contains a serine hydroxymethyltransferase (SHMT)-encoding gene. SHMT catalyzes the reversible cleavage of serine to form glycine and monocarbonic groups, essential in several biosynthetic pathways. SHMT of halotolerant bacteria is up-regulated under conditions of high salinity, resulting in an increased salinity tolerance due to an accumulation of glycine betaine within the cell (Waditee-Sirisattha, Sittipol, Tanaka & Takabe 2012). Non-haemolytic *S. agalactiae* can infect a wide range of marine fishes (Bowater et al. 2012) and SHMT could potentially play a role in persistence within the marine environment.

Other fish-associated loci were located in putative PAI described in human *S. agalactiae* strains, with Loci 5 and 6 located in PAI VI and Locus 2 in PAI IV (Glaser et al. 2002; Herbert et al. 2005). Locus 2 occupied a region that corresponds to a cluster of genes that include either the virulence gene rib (e.g. in 2603V/R) or bca (e.g. in A909). These genes are mutually exclusive and form part of a 3-set genotyping system for *S. agalactiae* (Kong, Gowan, Martin, James & Gilbert 2002). In PCR-based screening of CC552 isolates for rib and bac, all isolates tested negative (Delannoy et al. 2013), which would be explained by the replacement of these genes by Locus 2. This locus is predicted to encode a cytoplasmic protein, but the function is unknown. Locus 3, which is located just outside PAI IV, contains a number of genes whose corresponding proteins are not found in *S. agalactiae* genomes other than CC7 and CC552; some of these, however, are well-conserved in other streptococci, including the fish-pathogenic species *Streptococcus ictaluri* and *Streptococcus iniae*, and species that affect other hosts, such as *Streptococcus suis* (pigs) and *Streptococcus canis* (dogs). The proteins encoded by this locus are involved in carbohydrate transport and metabolism and include the beta-galactosidase, GalA, an enzyme that catalyzes the hydrolysis of galactose-containing oligosaccharides. It also contains genes for all enzymes of the Leloir pathway (GalK, GalE, GalM and GalT), which is involved in the transport and degradation of galactose. These genes have been well-characterised in lactic acid bacteria (Grossiord, Vaughan, Luesink & de Vos 1998). Galactose is present in dairy products, but also in fish tissues like the brain, where it is a component of glycolipids and glycoproteins (Tocher 2003). The presence of these genes in meningoencephalitis-causing bacteria such as piscine *S. agalactiae* may therefore provide some metabolic advantages. In *S. thermophilus*, the primary role for Leloir pathway enzymes is to produce precursor sugars for assembly of exopolysaccharides (EPS; Levander & Rådström 2001). EPS are secreted externally and differ from the capsular polysaccharides (CPS) that are tightly-associated with the cell surface (Levander & Rådström 2001). The production of EPS in bacteria leads to a loose 'fluffy' pellet phenotype following centrifugation (Forde & Fitzgerald 2002). To our knowledge, EPS formation has not been describe in *S. agalactiae*, but isolates from CC552 do form fluffy pellets. Genes responsible for EPS production in *S. thermophilus* share a high level of homology with capsular polysaccharide (CPS) genes from *S. agalactiae* (Stingele, Neeser & Mollet 1996), suggesting a common origin of these genes. The *S. agalactiae* capsule is composed of numerous polysaccharides that include glucose, galactose and rhamnose (Cieslewicz, Chaffin, Glusman, Kasper, Madan, Rodrigues, Fahey, Wessels & Rubens 2005) and it is conceivable that enzymes encoded by Locus 3 play a role in the production of precursors involved in the capsule rather than EPS formation.

Although the functional relevance of putatively fish-specific genome content of CC552 strains remains to be determined, the reduced genome content of members of CC552 may well explain why their host range is restricted to poikilothermic animals. It seems unlikely that these strains, which are thermosensitive (limited to no growth up to 37° C.) and have undergone extensive niche restriction and genome reduction (Lopez-Sanchez et al. 2012) would revert to virulence for humans, a concern raised in the context of the use of doctor fish for pedicure (Verner-Jeffreys, Baker-Austin, Pond, Rimmer, Kerr, Stone, Griffin, White, Stinton, Denham, Leigh, Jones, Longshaw & Feist 2012). Conversely, acquisition of fish-associated virulence factors by strains with a primary homeothermic host range may pose a risk for emergence of additional strains with high virulence in fish. Epidemiological studies, MLST data and phylogenetic analysis have shown that ST7 and ST283 form part of a large group of amalgamated CCs that are primarily associated with carriage and infection in humans, implying that spill-over has occurred in the human-to-fish direction rather than vice versa (Delannoy et al. 2013; Liu et al. 2013). Fish-associated genes, particularly those detected in all piscine and CC7 isolates examined in the current study, could potentially be used as diagnostic markers to indicate the ability of *S. agalactiae* strains to cause disease in fish.

In conclusion, the genome of fish-derived strain STIR-CD-17 (ST260) showed evidence of niche restriction, which is in agreement with epidemiological observations. Comparison of the ST260 genome with genomes of *S. agalactiae* strains derived from humans and cattle led to identification of 8 loci that were found only in the fish-derived strains, including a locus encoding the Leloir pathway. Additional in silico analysis and PCR-based screening of a collection of isolates from humans, cattle, fish and sea mammals showed that elements of those loci are shared by all *S. agalactiae* CCs known to infect fish (CC7, CC552), regardless of host or country of origin, whereas they are absent from CCs that have not been detected in fish. The 8 loci are also absent from strain MRI Z1-201 (ST23), which failed to cause morbidity or mortality after intraperitoneal injection in tilapia.

Tables

TABLE 2

*Streptococcus agalactiae* genome sequences included in genomic comparison.

| Host | Strain | Source | CC | ST | Serotype | Accession Number | References |
|---|---|---|---|---|---|---|---|
| Human | CJB111 | Blood | 1 | 1 | V | NZ_AAJQ00000000 | Tettelin et al. 2005 |
| | H36B | Umbilicus | 7 | 6 | Ib | NZ_AAJS00000000 | Tettelin et al. 2005 |
| | A909 | Umbilicus | 7 | 7 | Ia | NC_007432 | Tettelin et al. 2005 |
| | COH1 | Blood | 17 | 17 | III | NZ_AAJR00000000 | Tettelin et al. 2005 |
| | 18RS21 | Umbilicus | 19 | 19 | II | NZ_AAJO00000000 | Tettelin et al. 2005 |
| | 2603V/R | Unknown | 19 | 110 | V | NC_004116 | Tettelin et al. 2002 |
| | 515 | Cerebrospinal fluid | 23 | 23 | Ia | NZ_AAJP00000000 | Tettelin et al. 2005 |
| Bovine | ATCC 13813 | Milk | 67 | *61 | II | AEQQ00000000 | N/A |
| | FSL S3-026 | Milk | 67 | 67 | III | AEXT00000001 | Richards etal. 2011 |
| Unknown | NEM316 | Unknown | 23 | 23 | III | NC_004368 | Glaser etal. 2002; Sørensen etal. 2010 |

*The bovine strain ATCC 13813 has been typed by MLST PCR as ST61 (Evans et al. 2008), but it was also reported by Liu et al. (2013) as S1337. ST337 and ST61 differ at locus glcK (allele number 2 and 1 respectively), which is the only locus that we could not investigate from the genome due to its incompleteness (in between 2 contigs). The typing result from Evans et al. (2008) is retained here. N/A, not applicable.

TABLE 3

Distribution of adhesins, invasins and immune evasins in *Streptococcus agalactiae* highly-pathogenic (STIR-CD-17, ST260, serotype 1b) or non-pathogenic (MRI Z1-201, ST23, serotype 1a; NEM316, ST23, serotype III; Mian et al., 2009) to fish. Locus tags are provided when available (annotated genomes).

| Virulence factors | Related gene(s) | STIR-CD-17 | MRI Z1-201 | NEM316 |
|---|---|---|---|---|
| *Adhesins* | | | | |
| Fibrinogen-binding proteins | fbsA | M3M_07935 | | GBS1087 |
| | fbsB | | + | GBS0850 |
| Fibronectin-binding protein | pavA | M3M_03075 | + | GBS1263 |
| Serin-rich protein | srr1 | M3M_05192 | + | GBS1529 |
| | srr2 | | – | |
| Immunogenic bacterial adhesin | bibA | M3M_09338 | +* | GBS2018 |
| Pilus island PI-1 | PI-1 backbone protein | | – | |
| | PI-1 ancillary protein 2 | | – | |
| | Sortase family protein | | – | |
| | Sortase family protein | | – | |
| | PI-1 ancillary protein 1 | | – | |
| Pilus Island PI-2a | PI-2a ancillary protein 2 | | + | GBS1474 |
| | Sortase family protein | | + | GBS1475 |
| | Sortase family protein | | + | GBS1476 |
| | PI-2a backbone protein | | + | GBS1477 |
| | PI-2a ancillary protein 1 | | + | GBS1478 |
| Pilus Island PI-2b | PI-2b ancillary protein 1 | M3M_06299 | – | |
| | PI-2b backbone protein | M3M_06294* | – | |
| | Sortase family protein | Pseudo* | – | |
| | PI-2b ancillary protein 2 | M3M_06274 | – | |
| | Sortase family protein | M3M_06269 | – | |
| Laminin-binding protein | lmb | | + | GBS1307 |
| *Invasins* | | | | |
| β-hemolysin/cytolysin | cyIX | | + | GBS0644 |
| | cyID | | + | GBS0645 |
| | cyIG | | + | GBS0646 |

TABLE 3-continued

Distribution of adhesins, invasins and immune evasins in *Streptococcus agalactiae* highly-pathogenic (STIR-CD-17, ST260, serotype 1b) or non-pathogenic (MRI Z1-201, ST23, serotype 1a; NEM316, ST23, serotype III; Mian et al., 2009) to fish. Locus tags are provided when available (annotated genomes).

| Virulence factors | Related gene(s) | STIR-CD-17 | MRI Z1-201 | NEM316 |
|---|---|---|---|---|
| | acpC | | + | GBS0647 |
| | cylZ | | + | GBS0648 |
| | cylA | M3M_00355+ | + | GBS0649 |
| | cylB | M3M_00350 | + | GBS0650 |
| | cylE | M3M_00345+ | + | GBS0651 |
| | cylF | | + | GBS0652 |
| | cylI | | + | GBS0653 |
| | cylJ | | + | GBS0654 |
| | cylK | | + | GBS0655 |
| CAMP factor | cfb | M3M_09048 | + | GBS2000 |
| Hyaluronatelyase | hylB | M3M_03035 | + | GBS1270 |
| Surface protein rib | rib | | − | GBS0470 |
| C-α protein | bca | | − | |
| Immune evasins | | | | |
| Capsule | cps and neu genes cluster | M3M_08948-09023 | + | GBS1233-1247 |
| Penicillin-binding protein 1A | pbp1A/ponA | M3M_06939 | + | GBS0288 |
| Serine protease cspA | cspA | Pseudo* | + | GBS2008 |
| C5a peptidase | scpB | — | + | GBS1308 |
| C-β protein | bac | — | − | |

*Partial gene sequence, or pseudogenes due to the introduction of stop codons.
+Genes partially present due to sequence deletion.

TABLE 4

Primer pairs for putatively fish-specific† or fish-associated‡ genes of *Streptococcus agalactiae*.

| Host association | Target | Locus tag | Primers | Tm (° C.) |
|---|---|---|---|---|
| Fish-specific | Beta-hydroxyacyl dehydratase FabA/FabZ | M3M_04280 | 71-AAATAATCCGATTGTTCCTG-91 | 51.2 |
| | | | 346-ATATACTATAAA1TTCCCTTCTAA-321 | 50.8 |
| | Putative RecB family exonuclease (cas4) | M3M_01062 | 5-CTATGCCGAAGATGATTATTTG-28 | 54.7 |
| | | | 491-CTTCTTGGCGTAGTTCCTCAGTA-467 | 60.6 |
| Fish-associated | Galactokinase | M3M_01167 | 466-AAATCGGCAAGCAGACAGAAAATGAAT-494 | 60.4 |
| | | | 1041-GCAATAGCACAACCGCCAAAACC-1017 | 62.4 |
| | Alpha galactosidase | M3M_01172 | 663-AAGGGTGCTAGTAGTGCCGAACATAAT-691 | 63.4 |
| | | | 1113-AACCAGCCATCATCCATAACAAAAAGT-1085 | 60.4 |
| | Sugar ABC transporter permease | M3M_01182 | 489-ATTGGTATTTGGAGCACTGTAGG-513 | 58.9 |
| | | | 740-TCTTATTATAGGCCGGACTTGTA-716 | 57.1 |

†limited to CC552 strains
‡limited to CC552 and CC7

TABLE 5

Distribution of putatively fish-specific (found in CC552 only) and fish-associated (found in CC7 and CC552) genes across a range of host species, clonal complexes (CC) and sequence types (ST) of *Streptococcus agalactiae* based on PCR or in silico analysis. For each profile and epidemiologically independent source, the number of isolates is shown.

| | Marker | | | | | | | | | | | |
|---|---|---|---|---|---|---|---|---|---|---|---|---|
| Profile | 4280 | 1062 | 1167 | 1172 | 1182 | Host | Country | (sub)CC | ST | Method | Comment | Isolates |
| 1 | 0 | 0 | 0 | 0 | 0 | Cattle | Denmark | 1 | 1 | PCR | | 1 |
| 1 | 0 | 0 | 0 | 0 | 0 | Cattle | Denmark | 1 | 1 | PCR | | 2 |
| 1 | 0 | 0 | 0 | 0 | 0 | Human | Unknow | 1 | 1 | In silico | | 1 |
| 1 | 0 | 0 | 0 | 0 | 0 | Cattle | Denmark | 1 | 478 | PCR | | 1 |
| 1 | 0 | 0 | 0 | 0 | 0 | Human | Unknow | 17 | 17 | In silico | | 1 |
| 1 | 0 | 0 | 0 | 0 | 0 | Cattle | Denmark | 19 | 19 | PCR | | 11 |
| 1 | 0 | 0 | 0 | 0 | 0 | Human | USA | 19 | 19 | In silico | | 1 |
| 1 | 0 | 0 | 0 | 0 | 0 | Cattle | Denmark | 19 | 44 | PCR | | 1 |

TABLE 5-continued

Distribution of putatively fish-specific (found in CC552 only) and fish-associated (found in CC7 and CC552) genes across a range of host species, clonal complexes (CC) and sequence types (ST) of *Streptococcus agalactiae* based on PCR or in silico analysis. For each profile and epidemiologically independent source, the number of isolates is shown.

| Profile | Marker 4280 | 1062 | 1167 | 1172 | 1182 | Host | Country | (sub)CC | ST | Method | Comment | Isolates |
|---|---|---|---|---|---|---|---|---|---|---|---|---|
| 1 | 0 | 0 | 0 | 0 | 0 | Human | Unknow | 19 | 110 | In silico | | 1 |
| 1 | 0 | 0 | 0 | 0 | 0 | Cattle | Denmark | 23 | 23 | PCR | | 1 |
| 1 | 0 | 0 | 0 | 0 | 0 | Human | Unknow | 23 | 23 | In silico | | 1 |
| 1 | 0 | 0 | 0 | 0 | 0 | Seal | UK | 23 | 23 | PCR | | 1 |
| 1 | 0 | 0 | 0 | 0 | 0 | Seal | UK | 23 | 23 | PCR | | 1 |
| 1 | 0 | 0 | 0 | 0 | 0 | Seal | UK | 23 | 23 | PCR | | 1 |
| 1 | 0 | 0 | 0 | 0 | 0 | Seal | UK | 23 | 23 | PCR | | 1 |
| 1 | 0 | 0 | 0 | 0 | 0 | Seal | UK | 23 | 23 | PCR | | 1 |
| 1 | 0 | 0 | 0 | 0 | 0 | Unknown | Unknown | 23 | 23 | In silico | NEM316 | 1 |
| 1 | 0 | 0 | 0 | 0 | 0 | Cattle | Denmark | 23 | 199 | PCR | | 1 |
| 1 | 0 | 0 | 0 | 0 | 0 | Cattle | USA | 67 | 67 | In silico | FSL S3-026 | 1 |
| 1 | 0 | 0 | 0 | 0 | 0 | Cattle | USA | 67 | 337 | In silico | ATCC13831 | 1 |
| 2 | 0 | 0 | 1 | 1 | 1 | Cattle | Denmark | 1 | 1 | PCR | | 1 |
| 2 | 0 | 0 | 1 | 1 | 1 | Human | USA | 7 | 6 | PCR | H36B | 1 |
| 2 | 0 | 0 | 1 | 1 | 1 | Fish | Thailand | 7 | 7 | PCR | | 1 |
| 2 | 0 | 0 | 1 | 1 | 1 | Fish | Chain | 7 | 7 | PCR | ZQ0910 | 1 |
| 2 | 0 | 0 | 1 | 1 | 1 | Fish | China | 7 | 7 | PCR | FG201008-001 | 1 |
| 2 | 0 | 0 | 1 | 1 | 1 | Human | Unknown | 7 | 7 | PCR | A909 | 1 |
| 2 | 0 | 0 | 1 | 1 | 1 | Fish | Thailand | 7 | 500 | PCR | | 1 |
| 2 | 0 | 0 | 1 | 1 | 1 | Fish | Thailand | 7 | 500 | PCR | | 1 |
| 3 | 0 | 1 | 1 | 1 | 1 | Fish | Thailand | 7 | 1 | PCR | | 1 |
| 3 | 0 | 1 | 1 | 1 | 1 | Fish | Thailand | 7 | 1 | PCR | | 1 |
| 3 | 0 | 1 | 1 | 1 | 1 | Fish | Thailand | 7 | 1 | PCR | | 1 |
| 3 | 0 | 1 | 1 | 1 | 1 | Fish | Thailand | 7 | 283 | PCR | | 1 |
| 3 | 0 | 1 | 1 | 1 | 1 | Dolphin | UK | 7 | 399 | PCR | | 1 |
| 3 | 0 | 1 | 1 | 1 | 1 | Fish | Vietnam | 7 | 491 | PCR | | 1 |
| 3 | 0 | 1 | 1 | 1 | 1 | Fish | Brasil | 552 | 553 | In silico | SA20-06 | 1 |
| 4 | 1 | 0 | 1 | 1 | 1 | Fish | Kuwait | 7 | 7 | PCR | | 5 |
| 4 | 1 | 0 | 1 | 1 | 1 | Fish | Australia | 552 | 261 | PCR | | 1 |
| 4 | 1 | 0 | 1 | 1 | 1 | Fish | Australia | 552 | 261 | PCR | | 1 |
| 4 | 1 | 0 | 1 | 1 | 1 | Fish | Australia | 552 | 261 | OCR | | 1 |
| 4 | 1 | 0 | 1 | 1 | 1 | Fish | Belgium | 552 | 261 | PCR | | 1 |
| 5 | 1 | 1 | 1 | 1 | 1 | Fish | Honduras | 552 | 260 | PCR | Incl. STIR-CD-17 | 4 |
| 5 | 1 | 1 | 1 | 1 | 1 | Fish | Columbia | 552 | 260 | PCR | | 1 |
| 5 | 1 | 1 | 1 | 1 | 1 | Fish | Cost Rica | 552 | 260 | PCR | | 4 |

REFERENCES

Amborski R. L., Snider, T. G., Thune, R. L. & Culley, D. D. J. (1983) A non-hemolytic, group B *Streptococcus* infection of cultured bullfrogs, *Rana catesbeiana*, in Brazil. *Journal of Wildlife Diseases* 19, 180-184.

Bishop E. J., Shilton, C., Benedict, S., Kong, F., Gilbert, G. L., Gal, D., Godoy, D., Spratt, B. G. & Currie, B. J. (2007) Necrotizing fasciitis in captive juvenile *Crocodylus porosus* caused by *Streptococcus agalactiae*: an outbreak and review of the animal and human literature. *Epidemiology and Infection* 135, 1248-1255.

Bowater R. O., Forbes-Faulkner, J., Anderson, I. G., Condon, K., Robinson, B., Kong, F., Gilbert, G. L., Reynolds, A., Hyland, S., McPherson, G., Brien, J. O. & Blyde, D. (2012) Natural outbreak of *Streptococcus agalactiae* (GBS) infection in wild giant Queensland grouper, *Epinephelus lanceolatus* (Bloch), and other wild fish in northern Queensland, Australia. *Journal of Fish Diseases* 35, 173-186.

Brochet M., Couve, E., Zouine, M., Vallaeys, T., Rusniok, C., Lamy, M., Buchrieser, C., Trieu-Cuot, P., Kunst, F., Poyart, C. & Glaser, P. (2006) Genomic diversity and evolution within the species *Streptococcus agalactiae*. *Microbes and Infection* 8, 1227-1243.

Carver T., Berriman, M., Tivey, A., Patel, C., Bohme, U., Barrell, B. G., Parkhill, J. & Rajandream, M. (2008) Artemis and ACT: viewing, annotating and comparing sequences stored in a relational database. *Bioinformatics* 24, 2672-2676.

Christensen J. J. & Facklam, R. R. (2001) *Granulicatella* and *Abiotrophia* species from human clinical specimens. *Journal of clinical microbiology* 39, 3520-3523.

Cieslewicz M. J., Chaffin, D., Glusman, G., Kasper, D., Madan, A., Rodrigues, S., Fahey, J., Wessels, M. R. & Rubens, C. E. (2005) Structural and genetic diversity of Group B *Streptococcus* capsular polysaccharides. *Infection and Immunity* 73, 3096-3103.

Crumlish M., Thanh, P. C., Koesling, J Tung, V. T. & Gravningen, K. (2010) Experimental challenge studies in Vietnamese catfish, *Pangasianodon hypophthalmus* (Sauvage), exposed to *Edwardsiella ictaluri* and *Aeromonas hydrophila*. *Journal of Fish Diseases* 33, 717-722.

Delannoy C. M. J., Zadoks, R. N., Lainson, F. A., Ferguson, H. W., Crumlish, M., Turnbull, J. F. & Fontaine, M. C. (2012) Draft genome sequence of a nonhemolytic fish-pathogenic *Streptococcus agalactiae* strain. *Journal of Bacteriology* 194, 6341-6342.

Delannoy C. M. J., Crumlish, M., Fontaine, M., Pollock, J., Foster, G., Dagleish, M., Turnbull, J. & Zadoks, R. (2013) Human *Streptococcus agalactiae* strains in aquatic mammals and fish. *BMC Microbiology* 13, 41.

Eldar A., Bejerano, Y., Livoff, A., Horovitcz, A. & Bercovier, H. (1995) Experimental streptococcal meningo-encephalitis in cultured fish. *Veterinary microbiology* 43, 33-40.

Elliott J. A., Facklam, R. R. & Richter, C. B. (1990) Whole-cell protein patterns of nonhemolytic group B, type Ib, streptococci isolated from humans, mice, cattle, frogs, and fish. *Journal of Clinical Microbiology* 28, 628-630.

Evans J. J., Bohnsack, J. F., Klesius, P. H., Whiting, A. A., Garcia, J. C., Shoemaker, C. A. & Takahashi, S. (2008) Phylogenetic relationships among *Streptococcus agalactiae* isolated from piscine, dolphin, bovine and human sources: a dolphin and piscine lineage associated with a fish epidemic in Kuwait is also associated with human neonatal infections in Japan. *Journal of Medical Microbiology* 57, 1369-1376.

Feil E. J., Li, B. C., Aanensen, D. M., Hanage, W. P. & Spratt, B. G. (2004) eBURST: inferring patterns of evolutionary descent among clusters of related bacterial genotypes from multilocus sequence typing data. *Journal of Bacteriology* 186, 1518-1530.

Forde A. & Fitzgerald, G. F. (2003) Molecular organization of exopolysaccharide (EPS) encoding genes on the lactococcal bacteriophage adsorption blocking plasmid, pCI658. *Plasmid* 49, 130-142.

Geng Y., Wang, K. Y., Huang, X. L., Chen, D. F., Li, C. W., Ren, S. Y., Liao, Y. T., Zhou, Z. Y., Liu, Q. F., Du, Z. J. & Lai, W. M. (2012) *Streptococcus agalactiae*, an emerging pathogen for cultured Ya-Fish, *Schizothorax prenanti*, in China. *Transboundary and Emerging Diseases* 59, 369-375.

Glaser P., Rusniok, C., Buchrieser, C., Chevalier, F., Frangeul, L., Msadek, T., Zouine, M., Couve, E., Lalioui, L., Poyart, C., Trieu-Cuot, P. & Kunst, F. (2002) Genome sequence of *Streptococcus agalactiae*, a pathogen causing invasive neonatal disease. *Molecular Microbiology* 45, 1499-1513.

Grossiord B., Vaughan, E., E., Luesink, E. & de Vos, W., M. (1998) Genetics of galactose utilisation via the Leloir pathway in lactic acid bacteria. *Lait* 78, 77-84.

Halio S. B., Blumentals, I. I., Short, S. A., Merrill, B. M. & Kelly, R. M. (1996) Sequence, expression in *Escherichia coli*, and analysis of the gene encoding a novel intracellular protease (PfpI) from the hyperthermophilic archaeon *Pyrococcus furiosus*. *Journal of Bacteriology* 178, 2605-2612.

Herbert M., Beveridge, C., McCormick, D., Aten, E., Jones, N., Snyder, L. & Saunders, N. (2005) Genetic islands of *Streptococcus agalactiae* strains NEM316 and 2603VR and their presence in other Group B Streptococcal strains. *BMC Microbiology* 5, 31.

Huson D., Richter, D., Rausch, C., Dezulian, T., Franz, M. & Rupp, R. (2007) Dendroscope: An interactive viewer for large phylogenetic trees. *BMC Bioinformatics* 8, 460.

Ip M., Cheuk, E. S. C., Tsui, M. H. Y., Kong, F., Leung, T. N. & Gilbert, G. L. (2006) Identification of a *Streptococcus agalactiae* serotype III subtype 4 clone in association with adult invasive disease in Hong Kong. *Journal of Clinical Microbiology* 44, 4252-4254.

Jones N., Bohnsack, J. F., Takahashi, S., Oliver, K. A., Chan, M. S., Kunst, F., Glaser, P., Rusniok, C., Crook, D. W., Harding, R. M., Bisharat, N. & Spratt, B. G. (2003) Multilocus Sequence Typing System for Group B *Streptococcus*. *Journal of Clinical Microbiology* 41, 2530-2536.

Kong F., Gowan, S., Martin, D., James, G. & Gilbert, G. L. (2002) Molecular Profiles of Group B Streptococcal surface protein antigen genes: relationship to molecular serotypes. *Journal of clinical microbiology* 40, 620-626.

Laing C., Buchanan, C., Taboada, E., Zhang, Y., Kropinski, A., Villegas, A., Thomas, J. & Gannon, V. (2010) Pan-genome sequence analysis using Panseq: an online tool for the rapid analysis of core and accessory genomic regions. *BMC Bioinformatics* 11, 461.

Levander F. & Rådström, P. (2001) Requirement for phosphoglucomutase in exopolysaccharide biosynthesis in glucose- and lactose-utilizing *Streptococcus thermophilus*. *Applied and Environmental Microbiology* 67, 2734-2738.

Liu G., Zhang, W. & Lu, C. (2012) Complete genome sequence of *Streptococcus agalactiae* GD201008-001, isolated in China from Tilapia with meningoencephalitis. *Journal of Bacteriology* 194, 6653-6653.

Liu G., Zhang, W. & Lu, C. (2013) Comparative genomics analysis of *Streptococcus agalactiae* reveals that isolates from cultured tilapia in China are closely related to the human strain A909. *BMC Genomics* 14, 775.

Lopez-Sanchez M. J., Sauvage, E., Da Cunha, V., Clermont, D., Ratsima Hariniaina, E., Gonzalez-Zorn, B., Poyart, C., Rosinski-Chupin, I. & Glaser, P. (2012) The highly dynamic CRISPR1 system of *Streptococcus agalactiae* controls the diversity of its mobilome. *Molecular Microbiology* 85(6), 1057-1071.

Makarova K. S., Haft, D. H., Barrangou, R., Brouns, S. J. J., Charpentier, E., Horvath, P., Moineau, S., Mojica, F. J. M., Wolf, Y. I. & Yakunin, A. F. (2011) Evolution and classification of the CRISPR-Cas systems. *Nature Reviews Microbiology* 9, 467-477.

Manning S. D., Springman, A. C., Lehotzky, E., Lewis, M. A., Whittam, T. S. & Davies, H. D. (2009) Multilocus sequence types associated with neonatal Group B Streptococcal sepsis and meningitis in Canada. *Journal of Clinical Microbiology* 47, 1143-1148.

Mian G., Godoy, D., Leal, C., Yuhara, T., Costa, G. & Figueiredo, H. (2009) Aspects of the natural history and virulence of *S. agalactiae* infection in Nile tilapia. *Veterinary Microbiology* 136, 180-183.

Miles A. A., Misra, S. S. & Irwin, J. O. (1938) The estimation of the bactericidal power of the blood. *Epidemiology & Infection* 38, 732.

Milne I., Wright, F., Rowe, G., Marshall, D. F., Husmeier, D. & McGuire, G. (2004) TOPALi: software for automatic identification of recombinant sequences within DNA multiple alignments. *Bioinformatics* 20, 1806-1807.

Ohnishi Y., Yamazaki, H., Kato, J., Tomono, A. & Horinouchi, S. (2005) AdpA, a central transcriptional regulator in the A-factor regulatory cascade that leads to morphological development and secondary metabolism in *Streptomyces griseus*. *Bioscience, Biotechnology, and Biochemistry* 69, 431-439.

Pao S. S., Paulsen, I. T. & Saier, M. H. (1998) Major facilitator superfamily. *Microbiology and Molecular Biology Reviews* 62, 1-34.

Pasnik D. J., Evans, J. J., Klesius, P. H., Shoemaker, C. A. & Yeh, H. (2009) Pathogenicity of *Streptococcus ictaluri* to channel catfish. *Journal of Aquatic Animal Health* 21, 184-188.

Pereira U. P., Rodrigues, D. S., Hassan, S., Aburjaile, F., Soares, S. C., Ramos, R., Carneiro, A., Guimarães, L., Silva, d. A., Diniz, C., Barbosa, M., Gomes de Sá, P., Ali, A., Bakhtiar, S., Dorella, F., Zerlotini, A., Araújo, F., Leite, L., Oliveira, G., Miyoshi, A., Silva, A., Azevedo, V. & Figueiredo, H. (2013) Complete genome sequence of *Streptococcus agalactiae* strain SA20-06, a fish pathogen associated to meningoencephalitis outbreaks. *Standards in Genomic Sciences* 8, 188-197.

Rasko D., Myers, G. & Ravel, J. (2005) Visualization of comparative genomic analyses by BLAST score ratio. *BMC Bioinformatics* 6, 2.

Richards V. P., Lang, P., Pavinski Bitar, P. D., Lefébure, T., Schukken, Y. H., Zadoks, R. N. & Stanhope, M. J. (2011) Comparative genomics and the role of lateral gene transfer in the evolution of bovine adapted *Streptococcus agalactiae*. *Infection, Genetics and Evolution* 11, 1263-1275.

Ronquist F. & Huelsenbeck, J. P. (2003) MrBayes 3: Bayesian phylogenetic inference under mixed models. *Bioinformatics* 19, 1572-1574.

Rosinski-Chupin I., Sauvage, E., Mairey, B., Mangenot, S., Ma, L., Da Cunha, V., Rusniok, C., Bouchier, C., Barbe, V. & Glaser, P. (2013) Reductive evolution in *Streptococcus agalactiae* and the emergence of a host adapted lineage. *BMC Genomics* 14, 252.

Saunders N. J. & Snyder, L. A. (2002) The minimal mobile element. *Microbiology* 148, 3756-3760.

Shewmaker P. L., Camus, A. C., *Bailiff*, T., Steigerwalt, A. G., Morey, R. E. & Carvalho, M.d.G. S. (2007) *Streptococcus ictaluri* sp. nov., isolated from Channel Catfish *Ictalurus punctatus* broodstock. *International Journal of Systematic and Evolutionary Microbiology* 57, 1603-1606.

Sorensen U. B. S., Poulsen, K., Ghezzo, C., Margarit, I. & Kilian, M. (July/August 2010) Emergence and global dissemination of host-specific *Streptococcus agalactiae* clones. *mBio* 1, e00178-10-e00178-18.

Stingele F., Neeser, J. R. & Mollet, B. (1996) Identification and characterization of the eps (Exopolysaccharide) gene cluster from *Streptococcus thermophilus* Sfi6. *Journal of Bacteriology* 178, 1680-1690.

Tatusov R., Fedorova, N., Jackson, J., Jacobs, A., Kiryutin, B., Koonin, E., Krylov, D., Mazumder, R., Mekhedov, S., Nikolskaya, A., Rao, B. S., Smirnov, S., Sverdlov, A., Vasudevan, S., Wolf, Y., Yin, J. & Natale, D. (2003) The COG database: an updated version includes eukaryotes. *BMC Bioinformatics* 4, 41.

Tazi A., Disson, O., Bellais, S., Bouaboud, A., Dmytruk, N., Dramsi, S., Mistou, M., Khun, H., Mechler, C., Tardieux, I., Trieu-Cuot, P., Lecuit, M. & Poyart, C. (2010) The surface protein HvgA mediates group B *Streptococcus* hypervirulence and meningeal tropism in neonates. *The Journal of Experimental Medicine* 207, 2313-2322.

Tettelin H., Masignani, V., Cieslewicz, M. J., Donati, C., Medini, D., Ward, N. L., Angiuoli, S. V., Crabtree, J., Jones, A. L., Durkin, A. S., Deboy, R. T., Davidsen, T. M., Mora, M., Scarselli, M., Margarit, y. R., Peterson, J. D., Hauser, C. R., Sundaram, J. P., Nelson, W. C., Madupu, R., Brinkac, L. M., Dodson, R. J., Rosovitz, M. J., Sullivan, S. A., Daugherty, S. C., Haft, D. H., Selengut, J., Gwinn, M. L., Zhou, L., Zafar, N., Khouri, H., Radune, D., Dimitrov, G., Watkins, K., O'Connor, K., Smith, S., Utterback, T. R., White, O., Rubens, C. E., Grandi, G., Madoff, L. C., Kasper, D. L., Telford, J. L., Wessels, M. R., Rappuoli, R. & Fraser, C. M. (2005) Genome analysis of multiple pathogenic isolates of *Streptococcus agalactiae*: implications for the microbial "pan-genome". *Proceedings of the National Academy of Sciences USA* 102, 13950-13955.

Tettelin H., Masignani, V., Cieslewicz, M. J., Eisen, J. A., Peterson, S., Wessels, M. R., Paulsen, I. T., Nelson, K. E., Margarit, I., Read, T. D., Madoff, L. C., Wolf, A. M., Beanan, M. J., Brinkac, L. M., Daugherty, S. C., DeBoy, R. T., Durkin, A. S., Kolonay, J. F., Madupu, R., Lewis, M. R., Radune, D., Fedorova, N. B., Scanlan, D., Khouri, H., Mulligan, S., Carty, H. A., Cline, R. T., Van Aken, S., Gill, J., Scarselli, M., Mora, M., Iacobini, E. T., Brettoni, C., Galli, G., Mariani, M., Vegni, F., Maione, D., Rinaudo, D., Rappuoli, R., Telford, J. L., Kasper, D. L., Grandi, G. & Fraser, C. M. (2002) Complete genome sequence and comparative genomic analysis of an emerging human pathogen, serotype V *Streptococcus agalactiae*. *Proceedings of the National Academy of Sciences USA* 99, 12391-12396.

Tocher D. R. (2003) Metabolism and functions of lipids and fatty acids in teleost fish. *Reviews in Fisheries Science* 11, 107-184.

Verner-Jeffreys D. W., Baker-Austin, C., Pond, M. J., Rimmer, G. S., Kerr, R., Stone, D., Griffin, R., White, P., Stinton, N., Denham, K., Leigh, J., Jones, N., Longshaw, M. & Feist, S. W. (2012) Zoonotic disease pathogens in fish used for pedicure. *Emerging infectious diseases* 18, 1006-1008.

Waditee-Sirisattha R., Sittipol, D., Tanaka, Y. & Takabe, T. (2012) Overexpression of serine hydroxymethyltransferase from halotolerant cyanobacterium in *Escherichia coli* results in increased accumulation of choline precursors and enhanced salinity tolerance. *FEMS microbiology letters* 333, 46-53.

Wang B., Jian, J., Lu, Y., Cai, S., Huang, Y., Tang, J. & Wu, Z. (2012) Complete genome sequence of *Streptococcus agalactiae* ZQ0910, a pathogen causing meningoencephalitis in the GIFT strain of Nile tilapia (*Oreochromis niloticus*). *Journal of Bacteriology* 194, 5132-5133.

Yu N. Y., Wagner, J. R., Laird, M. R., Melli, G., Rey, S., Lo, R., Dao, P., Sahinalp, S. C., Ester, M. & Foster, L. J. (2010) PSORTb 3.0: improved protein subcellular localization prediction with refined localization subcategories and predictive capabilities for all prokaryotes. *Bioinformatics* 26, 1608-1615.

Zadoks R. N., Middleton, J. R., McDougall, S., Katholm, J. & Schukken, Y. H. (2011) Molecular epidemiology of mastitis pathogens of dairy cattle and comparative relevance to humans. *Journal of Mammary Gland Biology and Neoplasia* 1-16.

The invention claimed is:

1. A method of raising an immune response or treating or preventing a disease, condition or infection with a streptococcal aetiology, in a fish, said method comprising administering an animal in need thereof an immunogenic amount of an immunogenic composition or vaccine comprising an antigen having at least 90% sequence identity to the *S. agalactiae* antigen, sugar ABC transporter sugar-binding protein.

2. The method of claim 1, wherein the disease, condition or infection with a streptococcal aetiology is a disease, condition and/or infection caused or contributed to by *S. agalactiae*.

3. The method of claim 1, wherein the immunogenic composition or vaccine further comprises one or more *S. agalactiae* antigens selected from the group consisting of:
   an antigen having at least 90% sequence identity to the *S. agalactiae* antigen Alpha-galactosidase;
   (ii) an antigen having at least 90% sequence identity to the *S. agalactiae* antigen rhamnulose-1-phosphate aldolase;
   (iii) an antigen having at least 90% sequence identity to the *S. agalactiae* antigen aldose 1-epimerase;
   (iv) an antigen having at least 90% sequence identity to the *S. agalactiae* antigen galactose mutarotase;
   (v) an antigen having at least 90% sequence identity to the *S. agalactiae* antigen galactokinase;
   (vi) an antigen having at least 90% sequence identity to the *S. agalactiae* antigen D-galactose-1-phosphate uridyltransferase;
   (vii) an antigen having at least 90% sequence identity to the *S. agalactiae* antigen UDP-galactose 4-epimerase;
   (viii) an antigen having at least 90% sequence identity to the *S. agalactiae* antigen ABC transporter permease;
   (ix) an antigen having at least 90% sequence identity to the *S. agalactiae* antigen sugar ABC transporter permease;
   (x) an antigen having at least 90% sequence identity to the *S. agalactiae* antigen AraC family transcriptional regulator;
   (xi) an antigen having at least 90% sequence identity to the *S. agalactiae* antigen phosphotransferase system, galactitol-specific JIB component;
   (xii) an antigen having at least 90% sequence identity to the *S. agalactiae* antigen PTS system, galactitol-specific IIC component;
   (xiii) an antigen having at least 90% sequence identity to the *S. agalactiae* antigen PTS system, galactitol-specific IIA component;
   (xiv) an antigen having at least 90% sequence identity to the *S. agalactiae* antigen PTS system galactitol-specific enzyme JIB component;
   (xv) an antigen having at least 90% sequence identity to the *S. agalactiae* antigen PTS system IIA domain-containing protein.

4. The method of claim 3, wherein the disease, condition or infection with a streptococcal aetiology is a disease, condition and/or infection caused or contributed to by *S. agalactiae*.

* * * * *

UNITED STATES PATENT AND TRADEMARK OFFICE
CERTIFICATE OF CORRECTION

PATENT NO. : 10,786,560 B1
APPLICATION NO. : 15/508327
DATED : September 29, 2020
INVENTOR(S) : Fontaine et al.

Page 1 of 1

It is certified that error appears in the above-identified patent and that said Letters Patent is hereby corrected as shown below:

On the Title Page

Item (30) Foreign Application Priority Data: Please correct "1415602" to read -- 1415602.0 --

In the Specification

Column 30, Line 6: Please correct "$10^6$ cfu" to read -- $10^5$ cfu --

Column 31, Line 19: Please correct "mmV" to read -- rnmV --

In the Claims

Column 51, Line 17, Claim 3: Please correct "an antigen" to read -- (i) an antigen --

Column 52, Line 13, Claim 3: Please correct "JIB" to read -- IIB --

Column 52, Line 22, Claim 3: Please correct "JIB" to read -- IIB --

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*